(12) United States Patent
Vu et al.

(10) Patent No.: US 10,969,360 B2
(45) Date of Patent: Apr. 6, 2021

(54) SOLID STATE ELECTRODES AND SENSORS HAVING REDOX ACTIVE SURFACE AREAS

(71) Applicant: Parker-Hannifin Corporation, Cleveland, OH (US)

(72) Inventors: Thang Huy Vu, San Jose, CA (US); Jai Krishnamurthy, Sunnyvale, CA (US); Srinivas Rao, Sunnyvale, CA (US)

(*) Notice: Subject to any disclaimer, the term of this patent is extended or adjusted under 35 U.S.C. 154(b) by 92 days.

(21) Appl. No.: 15/748,588

(22) PCT Filed: Jul. 29, 2016

(86) PCT No.: PCT/US2016/044907
§ 371 (c)(1),
(2) Date: Jan. 29, 2018

(87) PCT Pub. No.: WO2017/020019
PCT Pub. Date: Feb. 2, 2017

(65) Prior Publication Data
US 2019/0004004 A1    Jan. 3, 2019

Related U.S. Application Data

(60) Provisional application No. 62/198,580, filed on Jul. 29, 2015.

(51) Int. Cl.
G01N 27/327 (2006.01)
A61B 5/145 (2006.01)
(Continued)

(52) U.S. Cl.
CPC ....... *G01N 27/3277* (2013.01); *A61B 5/1468* (2013.01); *A61B 5/14539* (2013.01);
(Continued)

(58) Field of Classification Search
CPC .......... G01N 27/3277; G01N 27/4167; A61B 5/14539; A61B 5/1468
See application file for complete search history.

(56) References Cited

U.S. PATENT DOCUMENTS 6,541,268 B1 * 4/2003 Tonnessen ......... G01N 33/4925
436/133
7,132,837 B1 * 11/2006 Tao ........................ G01R 27/02
324/693
(Continued)

FOREIGN PATENT DOCUMENTS

CN      1390665 A      1/2003
CN    102439431 A      5/2012
(Continued)

OTHER PUBLICATIONS

U.S. Appl. No. 15/027,887, filed Jan. 29, 2015, Lee, US2015/0027887.
(Continued)

*Primary Examiner* — Luan V Van
*Assistant Examiner* — Caitlyn Mingyun Sun
(74) *Attorney, Agent, or Firm* — David R. Conklin; Kirton McConkie

(57) ABSTRACT

Solid-state electrodes comprising Redox Active Surface Areas for use in analyte sensing devices and various product platform devices.

19 Claims, 26 Drawing Sheets

(51) Int. Cl.
*A61B 5/1468* (2006.01)
*G01N 27/30* (2006.01)
*G01N 27/416* (2006.01)
*G01N 27/28* (2006.01)

(52) U.S. Cl.
CPC ....... *G01N 27/4167* (2013.01); *G01N 27/283* (2013.01); *G01N 27/302* (2013.01)

(56) References Cited

U.S. PATENT DOCUMENTS

| | | | | |
|---|---|---|---|---|
| 8,404,096 | B2* | 3/2013 | Purvis | C12Q 1/003 205/106 |
| 8,758,584 | B2* | 6/2014 | Kahn | G01N 27/3335 204/416 |
| 2003/0235817 | A1* | 12/2003 | Bartkowiak | A61B 5/14532 435/5 |
| 2008/0267823 | A1* | 10/2008 | Wang | C12Q 1/006 422/68.1 |
| 2009/0294277 | A1* | 12/2009 | Thomas | G01N 27/3272 204/192.1 |
| 2012/0055791 | A1* | 3/2012 | Leonard | G01N 27/4167 204/433 |
| 2012/0090995 | A1* | 4/2012 | Leonard | G01N 27/4166 204/406 |
| 2015/0027887 | A1* | 1/2015 | Lee | G01N 27/286 204/406 |

FOREIGN PATENT DOCUMENTS

CN 102449466 A 5/2012
WO WO-2013112767 A1 * 8/2013

OTHER PUBLICATIONS

U.S. Appl. No. 13/168,609, filed Jul. 4, 2013, Lee, US2013/0168609.

Daigle F et al: "Reagentless Tyrosinase Enzyme Electrodes: Effects of Enzyme Loading, Electrolyte pH, Ionic Strength, and Temperature", Analytical Chemistry, American Chemical Society, US, vol. 69, No. 20, Oct. 15, 1997, pp. 4108-4112, XP000724478, ISSN: 003-2700, DOI: 10.1021/AC970213F abstract; figure 1 p. 4108, right-hand column—p. 4109, left-hand column.

* cited by examiner

SOLID STATE ELECTRODES AND SENSORS HAVING REDOX ACTIVE SURFACE AREAS This application is a National Stage of International Application No. PCT/US2016/044907, filed Jul. 29, 2016, and entitled SOLID STATE ELECTRODES AND SENSORS HAVING REDOX ACTIVE SURFACE AREAS, which claims the benefit of United States Provisional Application No., 62/198,580, filed Jul. 29, 2015. This application claims priority to and incorporates herein by reference the above-referenced applications in their entirety.

BACKGROUND OF THE INVENTION

Field of the Invention

The present invention provides solid-state electrodes having optimized surface properties and geometries for use in electrochemical analysis, including pH measurement, as well as methods for making and using the materials of the invention, and the electrodes, sensors, and various product platform devices comprising them. Accordingly, the present invention relates to the fields of chemistry, and electrochemistry in particular, and to the field of analyte measurement, particularly pH measurement, and all the various fields where such measurements are made.

Description of Related Disclosures

Electrodes and analyte sensing devices based on analyte insensitive material ("AIM') and/or analyte sensitive material ("ASM") electrochemistry have previously been described. See, for example, U.S. Pat. Nos. 4,857,167; 5,223,117; 7,901,555; 8,177,958; 8,197,650; 8,506,779; 8,562,797; 8,877,037; 8,956,519; 8,961,754, and PCT Pub. Nos. 2010/026842, 2010/028726, 2011/045385, 2013/112767, and 2013/134582, 2014/106066, and 2015/035428, each of which is incorporated herein by reference. Electrodes utilizing the AIM ferrocene are described in Lafitte et al. (2008), *Electrochemistry Communications*, 10(12), 1831-1834; Hickman et al. (1991), *Science,* 252(5006), 688-691; Robinson and Lawrence (2006), *Electroanalysis,* 18 (2006) 677-683, and Robinson and Lawrence (2008), *Analytical Sciences* 24. 339-343.

Electrochemical sensors utilizing ASM/AIM and square wave voltammetry (SWV), sometimes called "voltammetric sensors," have been hailed as providing an opportunity for "calibration-free" sensing (meaning that the sensor does not have to calibrated by the end user), especially for pH measurement. In these sensors, a pH-sensitive signal, generated by the WE, and a pH-insensitive signal, generated by the IE, are generated contemporaneously by a given analyte using SWV methods. If the analyte is hydronium ion (for pH measurement), the ASM working electrode ("WE") changes potential in response to changes in hydronium ion concentration, whereas an ideal AIM for an indicator electrode ("IE") in a pH meter generates a potential that is constant, regardless of changes in the pH. Both of these potentials are measured relative to a reference electrode (RE) potential, as shown in FIG. 1.

With continued reference to FIG. 1, part A demonstrates a signal shift for the WE in the absence of a RE. The WE shift shown in part A in unable to be understood without reference data from the RE. Part B demonstrates a signal shift for the RE, thereby providing a context for the shift observed for the WE. Part C demonstrates the process for correcting signal drift for the WE and IE based on the signal shift data observed for the RE.

The difference or shift between the WE (i.e. ASM) and IE (i.e. AIM) signals can thus be correlated to pH, or other analyte, through the process of correcting signal drift. This difference ideally is independent of the absolute potential of the RE, which may be either a conventional reference electrode ("CRE", for example, a Ag/AgCl or $Hg_2Cl_2$ wire in a KCl solution) or a pseudo reference electrode ("PRE", for example, an exposed solid platinum, silver, or Ag/AgCl wire). Thus, for voltammetric sensors, changes in the RE have much less influence on the result than in conventional potentiometric pH sensors, which rely entirely on the stability and accuracy of the RE. Indeed, for voltammetric sensors, the simpler PRE may be used in place of a CRE.

The need for calibration-free sensor technology remains, however, as none of the sensors referred to as "calibration-free" have proven to be so in practice and/or exhibit deficiencies in accuracy and signal strength. For example, AIM electrodes (IEs) in the prior art based on ferrocene (Fc) typically exhibit weaker, relatively noisy signals. In addition, the IEs and WEs of the prior art generate relatively weak and/or unstable signals, particularly under rigorous test conditions. Further, the geometry and/or functional group density of these electrodes has not been optimized for the purpose of improving signal levels. The functional group density attainable is, moreover, usually lower than the density of reactive sites, which results in low signal levels and consequent uncertainty in electrode potential measurements.

Moreover, prior attempts to provide wholly solid-state wet-dry reversible pH sensors resulted in no commercial products; prior to the present invention, there still is no commercially available solid-state pH meter based on AIM/ASM solid-state technology. Prior attempts may have failed due to inability to generate sufficient signal strength at the WE, too rapid signal degradation during use or storage, insufficient sensitivity over a sufficiently broad pH range, and/or insufficient robustness for analyte samples or other conditions of use.

SUMMARY OF THE INVENTION

In one embodiment, the present invention provides solid-state electrodes having optimized surface properties and geometries for use in electrochemical analysis, including pH measurement, as well as methods for making and using the materials of the invention, and the electrodes, sensors, and various product platform devices comprising them. For example, some devices of the invention include planar surfaces comprising one or more solid-state electrodes having optimized surface properties and geometries configured to achieve an output signal in a desired range.

In one embodiment, a handheld pH measurement device is provided having a replaceable solid-state electrode comprising optimized geometries and surface properties. In one embodiment, a solid-state electrode is provided having materials and surface properties capable of producing an output signal in the range of from approximately 5 uA to approximately 400 uA. In one embodiment, a solid-state electrode is provided having materials and surface properties capable of producing an output signal in the range of from approximately 200 uA to approximately 5 mA.

The solid-state electrodes of the of the present invention comprise one or more redox-active materials ("RAM") and matrix materials, as described in U.S. patent application Ser. Nos. 13/812,135, 13/263,067, 14/758,491, 14/373,894, 14/383,873, and 14/758,491, and U.S. Pat. Nos. 8,877,037, 8,956,519, and 9,347,907, each of which is incorporated herein by reference, in its entirety. Some embodiments further include a pseudo reference electrode (PRE) comprising an exposed, sintered Ag/AgCl reference electrode. Some embodiments further comprise a counter electrode (CE) comprising stainless steel, Hastealloy, titanium coated platinum, or any inert metal or carbon material, such as a high density carbon material. In some embodiments, the CE material is selected based on an intended application, mechanical strength, and/or tarnish retardant properties of the material. For example, applications such as medical diagnostic equipment or drug delivery devices may require that the CE material comprise a noble metal.

Some embodiments of the invention further comprise a sensor having two or more solid-state electrodes comprising optimized electrode surface areas and/or RAM densities to provide a desired sensing ratio between the various electrodes. In one embodiment, a sensing ratio between two or more electrodes is optimized to improve overall sensitivity of the sensor device in which the electrodes are housed. In one embodiment, a sensing ration between two or more electrodes is optimized to improve performance of the device in which the electrodes are housed when the device is used to scan electrochemical parameters of a desired analyte. Accordingly, the invention relates to the fields of chemistry and electrochemistry in particular and to the field of analyte measurement, particularly pH measurement, and all the various fields where such measurements are made.

In a preferred embodiment, an optimized electrode of the invention is a small, compact, solid-state electrode that is wet-dry reversible having an ASM-based WE capable of generating a signal of at least 5 uA to no more than 400 uA and having an AIM-based IE in which the ASM of the WE and the AIM of the IE is incorporated into a cross-linked, hydrogel matrix non-covalently attached to a conductive substrate, such as carbon, doped silicon, modified silicon, or a conductive silicon derivative, or a conductive polymeric material. In one embodiment, the WE conductive substrate comprises at least one of graphite/carbon fiber epoxy, vinyl ester/carbon fiber epoxy, platinum, gold, silver, or any suitable composition comprising an inert metal.

In a first aspect, the present invention provides an analyte sensing device having one or more modified surfaces on which one or more optimized electrodes are located, wherein the one or more modified surfaces provides sufficient surface area to receive the one or more optimized electrodes, thereby providing an optimized analyte sensing device.

In a second aspect, an optimized electrode of the present invention comprises an exposed redox active surface area (RASA), wherein the exposed RASA is accessible to an analyte when the optimized electrode contacts a material or solution comprising the analyte. In some embodiments, the size and/or dimensions of the exposed RASA is optimized to produce an output signal in a desired range. In some embodiments, a thickness or density of a RAM applied to the exposed RASA is optimized to produce an output signal in a desired range. In some instances, the optimized electrode is a solid-state electrode. In some instances, a hybrid sensor comprises at least one solid-state electrode and at least one traditional, or non-solid-state electrode.

In a third aspect, the present invention provides an analyte sensing device having a sensor tip having one or modified surfaces, and each surface comprising one or more optimized electrodes, wherein each optimized electrode comprises an exposed RASA having a RAM. In a fourth aspect, the present invention provides a replaceable sensor module having one or more modified surfaces, and each surface comprising one or more optimized electrodes, wherein each optimized electrode comprises an exposed RASA having a RAM.

In a fifth aspect, the present invention provides an analyte sensing device having a receptacle for receiving a replaceable sensor module of the present invention. In some embodiments, the receptacle comprises a socket having a plurality of electrical contacts for operably receiving the replaceable sensor module. In one embodiment, the analyte sensing device comprises a handheld pH meter having a distal end comprising the socket, wherein the replaceable sensor module comprises a replaceable sensor tip having a plurality of electrical contacts for operable insertion within the socket.

In a sixth aspect, the present invention provides a product platform device having one or more optimized electrodes comprising an exposed RASA having an RAM. In some instances, a product platform device comprises food packaging. In some instances, a product platform device comprises a reaction vessel. In some instances, a product platform device comprises a sample plate, or a sample container, such as an Eppendorf® or Falcon® tube. In some instances, a product platform device comprises a planar structure, wherein the device is incorporated onto a wall or other planar surface of an item designed for use with an analyte. In some instances, a product platform device comprises a health diagnostic device having modified surfaces comprising optimized electrodes for detecting an analyte in a small liquid sample, such as a single droplet. In some instances, a product platform device comprises a handheld sensor. In some instances, the product platform device is intended for single-use. In one embodiment, the product platform device comprises one or more solid-state optimized electrodes. In one embodiment, the product platform device comprises a hybrid sensor comprising at least one solid-state optimized electrode and at least one traditional, or non-solid-state electrode.

In a seventh aspect, the present invention provides a reader comprising system electronics for receiving and/or compiling electrical signals from the one or more optimized electrodes. In some instances, the electrical signals are transmitted between the reader and the one or more optimized electrodes via Bluetooth signal. In some instances, the electrical signals are transmitted via a wired connection.

In an eighth aspect, the present invention provides an interactive sensor management system comprising a graphical user interface. In some instances, the management system maximizes the accuracy and longevity of the optimized electrodes by implementing application specific test profiles and internal standards based on an intended use for the optimized electrodes. In some instances, the management system adaptively learns a test environment to accurately predict and/or recommend optimal test profiles and internal standards for one or more product platform devices. In some instances, the management system uses at least one optimization technique (e.g., statistical) to improve the accuracy of collecting and analyzing data from one or more optimized electrodes. In some instances, the management system provides a user-friendly, intuitive display and one or more test status monitoring features, such as, for example, a warning alarm or a generated email. In some instances, the management system comprises one or more quality control features for detecting and reporting system or testing errors, such as, for example, sensor incompatibility, product development kit variations, or exceeding a threshold level or value. In some instances, the management system is configured to monitor and manage system level traceability. In some instances, the management system comprises features for executing scheduled test runs. In some instance, the management system is capable of remote operation.

DETAILED DESCRIPTION OF THE INVENTION

The present invention provides solid-state electrodes having optimized surface properties and geometries for use in electrochemical analysis, including pH measurement, as well as methods for making and using materials of the invention, and the electrodes, sensors, and various product platform devices comprising the same. Some embodiments of the invention further comprise one or more hybrid sensor comprising at least one optimized solid-state electrode and at least one traditional, or non-solid-state electrode. The optimized surface properties and geometries of the electrodes of the present invention, as well as the various product platform devices comprising these optimized electrodes overcome various limitations in the art.

Figure 1:
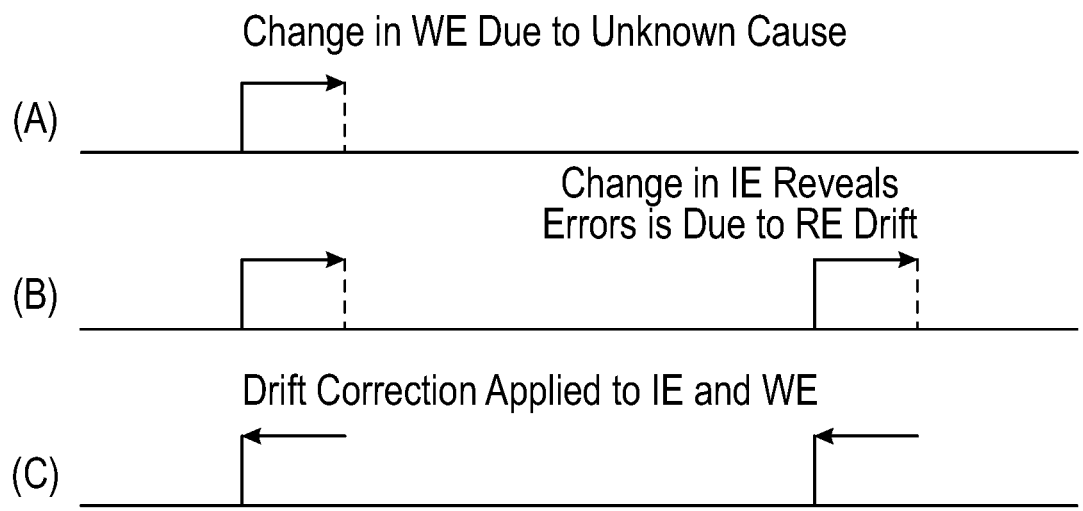
FIG. 1 shows schematically how, in an uncorrected voltammetric sensor, any drift in the RE potential results in a measurement error of an otherwise stable WE containing an analyte sensitive material (ASM) (illustrated in A of this Figure). This measurement error cannot be distinguished from a change in analyte concentration. If an analyte insensitive material (AIM) is used as an additional IE (illustrated in B of this Figure), any apparent drift must be attributed to the RE. Thus the drift in IE potential can be used to cancel the observed drift error in the working electrode (illustrated in C of this Figure). In this way, the difference in WE and IE potentials is effectively dissociated from changes in the properties or identity of the RE, and the sensor provides a more precise measure of the analyte.
Figure 2:
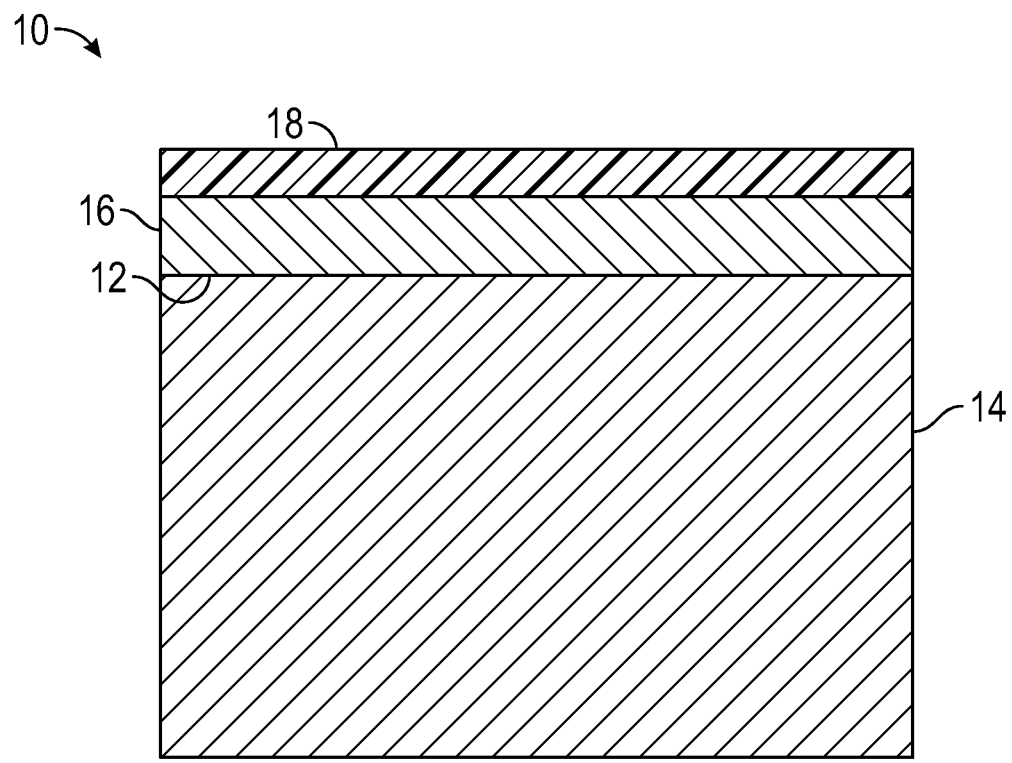
FIG. 2 is a cross-section side view of a sensor having a redox active surface area, a matrix coating, and a redox active material in accordance with a representative embodiment of the present invention.

Referring now to FIG. 2, a solid-state electrode 10 having an exposed RASA 12 is shown. Electrode 10 generally comprises a conductive substrate material 14. For example, in some instances substrate material 14 comprises a conductive material selected from the group consisting of carbon, doped silicon, modified silicon, a conductive silicon derivative, or a conductive polymeric material. In some embodiments, substrate material 14 further comprises a conductive material that has been doped with poly(3,4-ethylenedioxythiophene) (PEDOT), such as platinum, para-toluene sulfonate, polypyrrole, and other suitable polymers.

Conductive substrate material 14 comprises one or more RASAs 12. In one embodiment, RASA 12 comprises a portion of electrode substrate 14 that is exposed to and contacts an analyte when the electrode substrate is submerged in an analyte solution. As explained below, the size of the RASA 12 and the thickness of a redox active material ("RAM") 18 coated thereon directly relates to the current density of the electrode substrate. Thus, some embodiments of the present invention provide various electrode substrate configurations intended to maximize or otherwise provide a desired size for the RASA. In some instances, RASA 12 comprises a practical surface area comprising the RAM.

Size and shape of electrodes can influence measurement variation due to stray current fields and changes in current density. In some embodiments, the current density of a solid-state electrode of the present invention is altered by increasing or decreasing the size of the RASA of the electrode. Increasing the size of the RASA of the electrode decreases current density, while decreasing the size of the RASA increases current density. Generally, current density for a solid-state electrode is reduced at the cathode. Accordingly, in one embodiment a RASA of a negative electrode is increased to reduce current density. In one embodiment a RASA of a negative electrode is increased by two-fold.

In some embodiments, RASA 12 of substrate 14 comprises a matrix coating 16 that is non-covalently attached thereto. In some embodiments, matrix coating 16 comprises a cross-linked polyvinyl alcohol hydrogel material. In another embodiment, matrix coating 16 comprises a cross-linked acrylamide hydrogel material comprising vinyl ferrocene as a co-monomer, a cross-linked dimethyl acrylamide (DMAA) hydrogel material comprising vinyl ferrocene as a co-monomer, or any other cross-linked acrylamide hydrogel material. In some embodiments, matrix coating 16 comprises a polymer matrix. Some embodiments of the present invention further comprise any known matrix coating material that is compatible for use in accordance with the teachings of the present invention. Thus, RASA 12 may be coated with compatible matrix coating 16.

In some instances, matrix coating 16 further comprises one or more redox active materials (RAM) 18 covalently attached thereto. In some embodiments, a cross-linked hydrogel matrix material 16 further comprises a RAM 18 comprising at least one of an ASM and an AIM in accordance with the present teaching. Some embodiments of the present invention further comprise one or more RAM as is known in the art. Thus, matrix coating 16 may comprise any compatible RAM.

Figure 3:
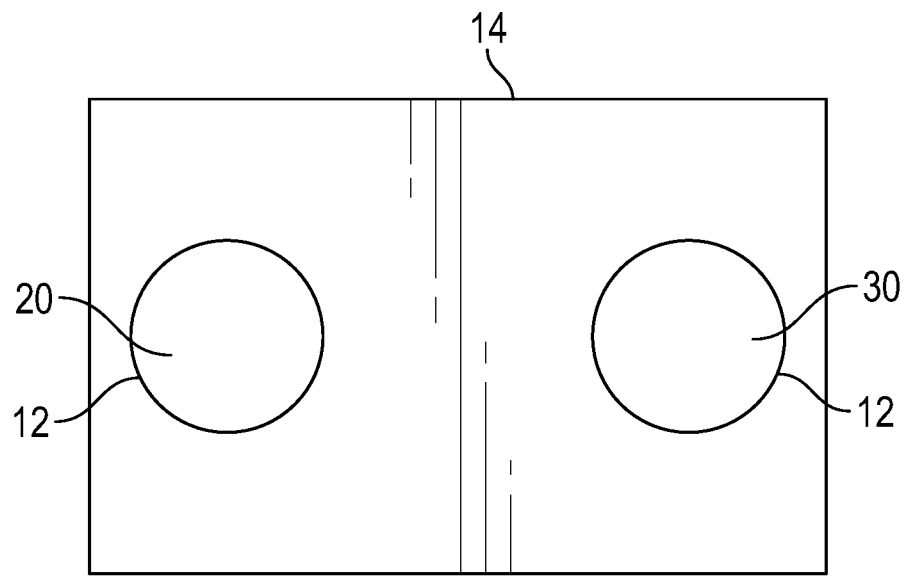
FIG. 3 is a top plan view of a sensor in accordance with a representative embodiment of the present invention.

In some embodiments, the size, shape, and/or placement of RASA 12 influences measurement variation for a pH meter device. With reference to FIG. 3, spatial spacing between a RASA 12 of a WE 20 and a CE 30 is necessary to ensure homogeneity of test media. Spatial separation may also be necessary to prevent electrical shorts. For planar sensor platforms, separation of adjacent RASAs, or spacing a RASA from another electrode surface by at least the diameter of the RASAs is desirable, wherein excessive separation may create problems for the transport characteristics of the analyte medium, which may affect measurement.

Figure 4:
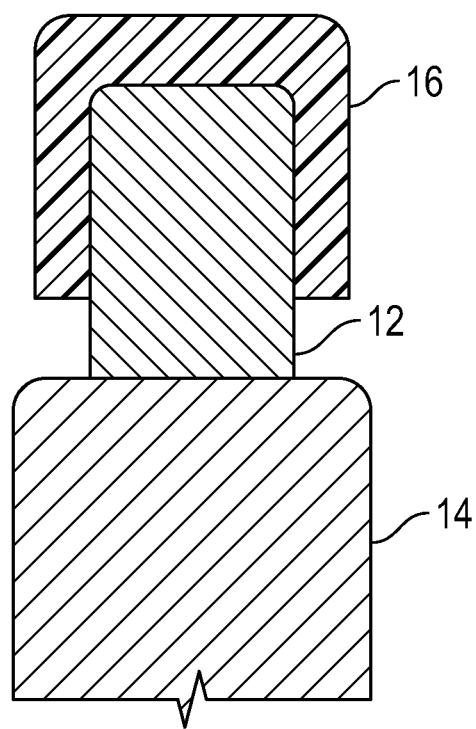
FIG. 4 is a cross-section side view of a sensor having a redox active surface area and matrix coating in accordance with a representative embodiment of the present invention.
Figure 5A:
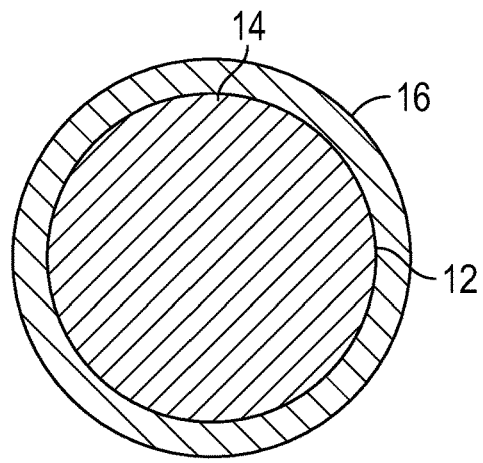
FIG. 5A is a cross-section top view of a sensor having an outer surface comprising a redox active surface area and a matrix coating disposed thereon in accordance with a representative embodiment of the present invention.
Figure 5B:
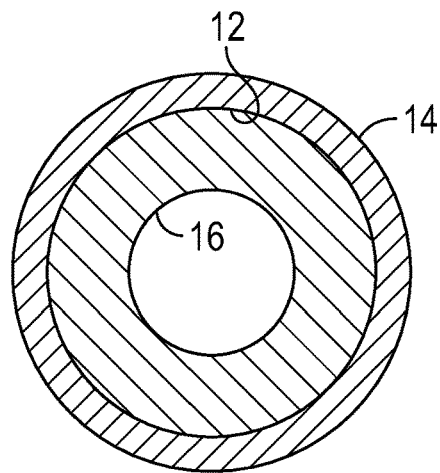
FIG. 5B is a cross-section top view of a sensor having an inner surface comprising a redox active surface area and a matrix coating disposed thereon in accordance with a representative embodiment of the present invention.
Figure 5C:
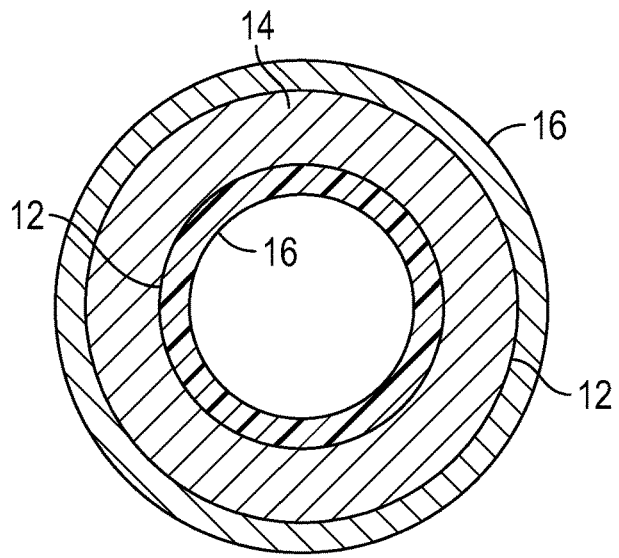
FIG. 5C is a cross-section top view of a sensor having an inner surface and an outer surface, each surface comprising a redox active surface area and matrix coating disposed thereon in accordance with a representative embodiment of the present invention.

Decreasing the current density of an electrode can extend the useful life of the electrode and/or sensor device. In some instances, current density for a RASA is decreased by decreasing the thickness of the matrix material thereon, which may extend the life of the electrode. In some instances, current density for a RASA is decreased by increasing the size of the RASA. For example, in some embodiments a RASA comprises a planar, two-dimensional surface area, as shown in FIG. 2. Accordingly, embodiments of the present invention provide RASAs having various shapes and configurations intended to adjust a current density of the electrode. For example, in some embodiments a RASA 12 comprises a three-dimensional surface area, as shown in FIG. 4. In some embodiments, a RASA 12 comprises an exterior surface, an interior surface, or exterior and interior surfaces of an electrode substrate, as shown in FIGS. 5A, 5B, and 5C, respectively.

The current density of an electrode substrate (expressed in $A/m^2$) may be increased or decreased by altering various physical parameters of the RASA. For example, solely increasing the size of the RASA by increasing the size or surface area of the electrode decreases the current density of the electrode, which may increase the usable life the electrode and/or sensor assembly, device or module. Conversely, increasing the size of the RASA by adding additional matrix coating and redox-active material will increase the current density. For example, increasing the thickness of the redox-active material of the RASA increases the current density. In some embodiments, the size of the electrode substrate RASA and/or the thickness of the matrix coating are selected to achieve a desired current density for the electrode. For example, in one embodiment the size of the electrode substrate RASA and/or the thickness of the matrix coating is selected to achieve a current density in the range of from approximately 1.0 $A/m^2$ to approximately 20.0 $A/m^2$, and in one embodiment to achieve a current density of approximately 8.8 $A/m^2$. In some embodiments, a RASA comprises a matrix coating having a thickness within the range of approximately 0.06 mm to approximately 0.25 mm, and preferably having a thickness of 0.123 mm+/−0.01 mm.

The RASA may further comprise a surface area selected to achieve a desired signal for the pH meter device. For example, in one embodiment the surface area of the RASA of at least one of a WE and an IE is selected to generate a signal within the range of not less than 5 µA to not greater than 400 µA, and preferably to generate an average signal of 100 µA, wherein the size of the RASA for the electrode is selected to be within the range of 8 $mm^2$ to 75 $mm^2$, and preferably in the range of 16.97 $mm^2$ to 38 $mm^2$, and further having an average current density of approximately 10 $A/m^2$. In one embodiment, one or more physical parameters of a RASA is selected to provide a current density of 20

A/m². In another embodiment, the area of the surface area of the CE is selected to generate a signal within in an effective range, wherein the size of the surface area of the CE is from 100 mm² to 400 mm², and preferably 283 mm², +/−10 mm². In another embodiment, the area of the RE RASA is selected to generate a signal within an effective range, wherein the size of the RASA of the RE is from 3.0 mm² to 15.0 mm², and preferably 7.0 mm², +/−0.1 mm².

In some embodiments, a RASA of an electrode is further optimized through frequent reconditioning. In one embodiment, the RASA of an electrode is reconditioned by applying an appropriate potential to the electrode. In another embodiment, the RASA of an electrode is reconditioned through a cleaning and/or sterilization process, such as rinsing with water, rinsing with hot water by stirring or clean-in-place, steam-in-place cleaning, or gamma radiation. In one embodiment, the present invention comprises a solid-state electrode that is electrochemically reversible, wherein the difference in forward and reverse current is approximately 59 mV.

In some embodiments, a sensor assembly, device or module of the present invention is further optimized through locating or positioning one or more solid-state electrodes at an optimal height within an analyte-containing solution. In one embodiment, an optimal height results in one or more solid-state electrodes being positioned in close proximity to an impeller located within the analyte-containing solution. In one embodiment, an optimal height results in one or more solid-state electrode being centrally positioned within an analyte-containing solution. In some embodiments, the position of one or more solid-state electrodes may be set and/or adjusted by manually moving and positioning the sensor assembly within analyte-containing solution. In another embodiment, a length of the sensor assembly (e.g., the length of a probe member comprising the one or more solid-state electrodes) may be adjusted to achieve a desired position of the one or more solid-state electrodes within the analyte-containing solution.

Electrode Sensor Construction

Electrode sensors of the present invention may comprise various structural and material elements known in the art. The following is a brief discussion of these various compatible elements in accordance with the present invention.

Electrode Design

Various embodiments of the present invention provide solid-state electrodes comprising RASA having an optimized level of surface texture, porosity, and/or three-dimensional tortuosity to ensure secure immobilization of one or more RAM thereto. In some instances, these features improve attachment and/or containment of a RAM hydrogel (AIM or ASM) without affecting the RAM's interaction with the analyte, in part benefitting from the highly permeable nature of the swollen hydrogel. These features also provide protection against physical damage to the RAM that may occur through contact or abrasion, or through detachment which might occur from repeated swelling and shrinking of the RAM hydrogel, as compared with the same material deposited on a smooth surface such as glassy carbon, or other metallic and non-metallic surfaces. In effect, the optimized mechanical properties of the textured or porous substrates of the present invention overcome the inherent fragility of RAM hydrogel to provide high structural integrity.

Any conductive substrate can be used as an electrode for the support, immobilization, and protection of RAM polymers and RAM hydrogels of the invention. These substrates may include carbon allotropes such as carbon fiber, porous graphite, macroporous carbon, mesoporous carbon, microporous carbon, nanoporous carbon, carbon nanofibers (made by carbon-coating on materials such as nanoporous alumina) and their composites; and nanotubes and their composite. Metal substrates may include nanoporous gold, platinum, and silver. Optimized screen-printed electrodes of the present invention may have a variety of surface coatings with desired roughness including mesoporous carbon, carbon nanofibers, carbon nanotubes, graphene, or carbon ink imprinted with micro- or nano-scale features such as channels or pores. Some porous conductive substrates of the present invention benefit further from very short signal pathways, thereby increasing signal capture efficiency.

Certain conductive polymers of the present invention are coated with a RAM hydrogel for use as an electrode substrate. Various embodiments of the present invention comprise polymer composites containing sufficient quantities of carbon allotrope or metal particles which have been engineered to render them conductive for use as supports for a RAM hydrogel. Suitable polymers for such composites include, for example, epoxy, polysulfone, polyethersulfone, polyphenylenesulfide, polypyrrole, polyvinylidenefluoride, other fluoropolymers or copolymers, and various vinyl polymers such as PVC, polystyrene, polymethylmethacrylate, and their derivatives and copolymers, cellulosic polymers, and silicone polymers.

Figure 6A:
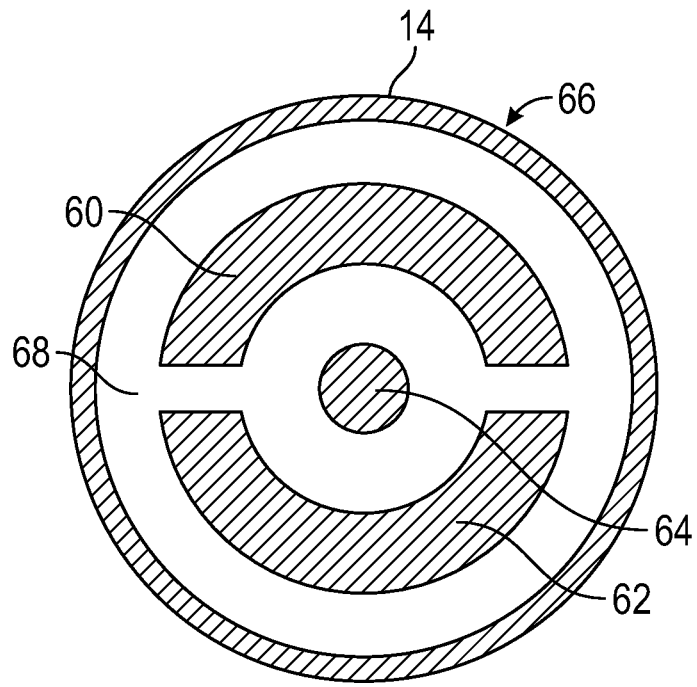
FIG. 6A is a plan end view of a sensor having a plurality of electrodes disposed thereon in a segmented arrangement in accordance with a representative embodiment of the present invention.
Figure 6B:
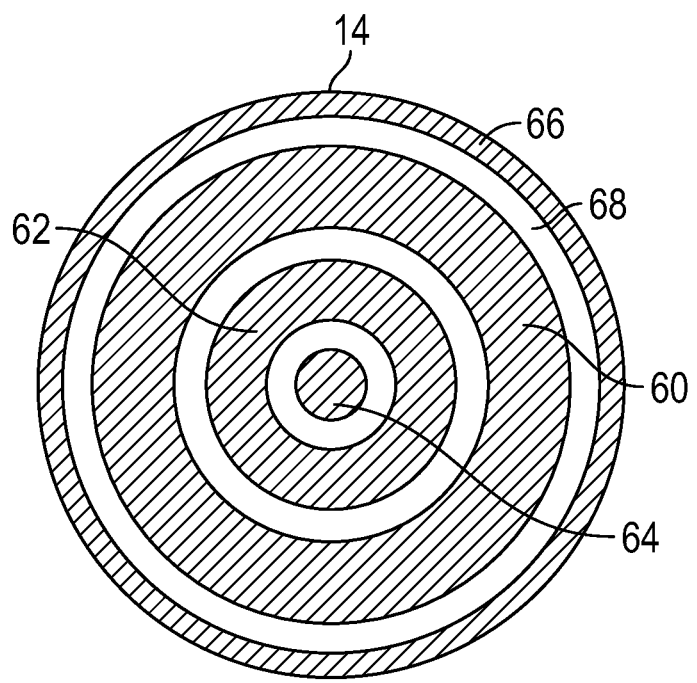
FIG. 6B is a plan end view of a sensor having a plurality of electrode disposed therein in a concentric arrangement in accordance with a representative embodiment of the present invention.

Various electrodes of this invention are made using rigid substrates such as various carbon composites, or on flexible conductive substrates (e.g. woven or nonwoven carbon fabric), or a nonconductive support film such as polyester, polyimide, polyolefin, etc. that has been rendered conductive with a conductive coating (such as carbon ink, indium tin oxide, silver, etc.). Some materials of the present invention are formed in various geometric patterns, which may include arrangements whereby compatible or companion electrodes, such as the CE and PRE, are arranged in close proximity. For example, the electrodes may be arranged as concentric rings, segments, and arrays, as shown in FIGS. 6A and 6B. Conductive coatings and electrodes derived therefrom allow sensors to be built in a wide range of form factors and dimensions.

Hydrogel Polymer Matrix

Some embodiments of the present invention comprise one or more hydrogel matrix materials in which a RAM (such as an ASM and/or AIM) is covalently attached to or stably entrapped therein. For example, in some embodiments the AIM of the IE (which can be or comprise a ferrocene derivative), and the ASM of the WE (which can be or comprise an anthraquinone derivative), is covalently linked to or physically entrapped within a highly swollen, cross-linked hydrophilic polymer matrix (a "hydrogel") that is not covalently linked to the conductive substrate, but rather adheres to the conductive via non-covalent bonding. The three-dimensional hydrogel structure accommodates a high concentration of the respective RAM. The high water permeability of the hydrogel ensures rapid interaction between the RAM and the analyte-containing sample being tested, thereby providing accelerated response. In various embodiments of the present invention, the RAM-containing hydrogel electrodes exhibit good wet-dry reversibility; retaining physical integrity upon drying and rapidly restoring redox activity upon rewetting. In some embodiments, the range of pH sensitivity of the sensor assemblies of the invention typically encompasses at least pH 2 to pH 10. Suitable hydrogels have been previously disclosed in PCT/US2015/035428, which is incorporated herein by reference.

Various solid-state electrodes of the present invention comprise a crosslinked hydrogel polymer matrix. Crosslinking provides an advantage in that the polymer can be polymerized in-situ, forming a robust network that physically attaches to the substrate, optionally penetrating substrates with certain degrees of porosity. Various matrix polymer materials discussed herein are crosslinked to provide the RAM hydrogel polymer. The characteristics of the polymerized monomers determine the specific type of hydrogel polymer. For example, in instances where the monomers or co-monomers comprise an AIM (such as an Fc derivative), the crosslinked polymer material may be termed an "AIM hydrogel".

In some embodiments, suitable crosslinkers comprise molecules having two polymerizable groups. Both the mol % RAM and mol % crosslinker are determined by the stoichiometric amounts of monomers used, assuming the polymerization reaction goes to completion and all monomers are incorporated into the polymer chain.

For some solid-state electrodes of the present invention, hydrogel polymers are formed by copolymerization of one or more hydrophilic co-monomers, at least one of which co-monomers is bi- or multi-functional. Bi- or multi-functional co-monomers are capable of forming crosslinks upon polymerization, and are referred to herein as "crosslinkers". In some embodiments, copolymerization of these components yields a hydrogel that provides an electrode that exhibits a pH-insensitive signal under SWV operating conditions.

Some solid-state electrodes of the present invention comprise a PVA-Fc hydrogel polymer matrix material that is crosslinked using one or more chemical crosslinkers selected from the group consisting of glutaraldehyde (or other dialdehydes), tetraethylorthosilicate (TEOS), boric acid, dicarboxylic acids, toluene diisocyanate, acrolien, polyacrylic acid, poly(methylvinyl ether-alt-MA), TEA, succinic anhydride, and maleic anhydride. In some embodiments, one or more of these chemical crosslinkers may be used to crosslink PVA. In some instances, a chemical crosslinker comprises a combination of glutaraldehyde and TEOS. In some instances, a suitable chemical crosslinker comprises a combination of toluene diisocyanate and one of acrolien, polyacrylic acid, poly(methylvinyl ether-alt-MA), TEA, succinic andydride, or maleic anhydride. In some instances, a PVA, PVA-AQ, or PVA-Fc hydrogel polymer matrix material of the present invention is provided via thermal or radiation crosslinking. Non-limiting examples of thermal and non-thermal chemical crosslinking reactions of the present invention are shown in Table 1.

TABLE 1

PVA Chemical Crosslinking

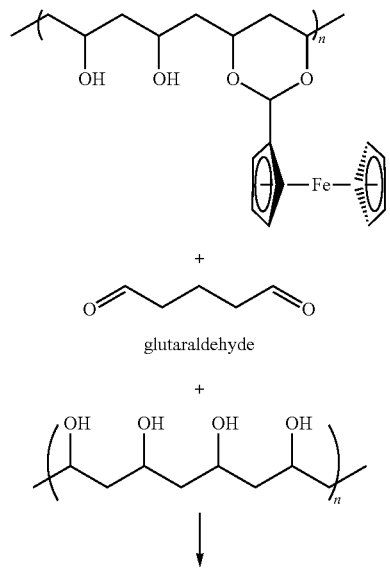

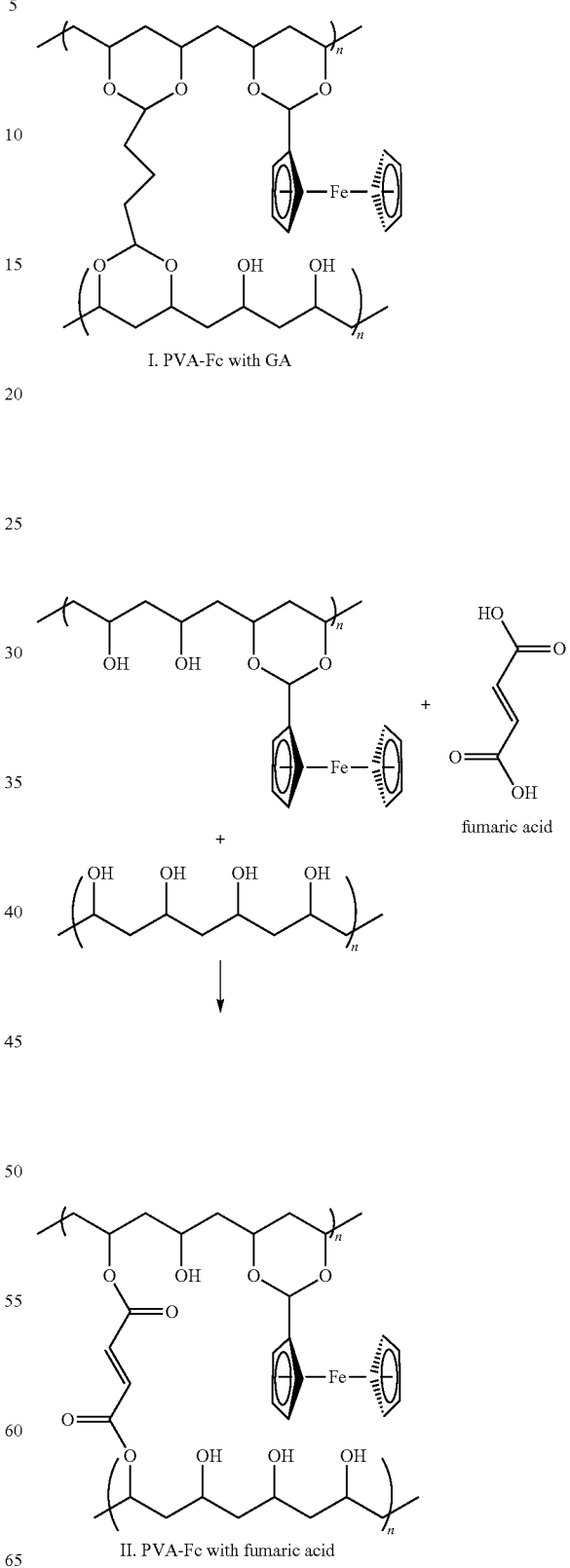

I. PVA-Fc with GA

II. PVA-Fc with fumaric acid

TABLE 1-continued

PVA Chemical Crosslinking

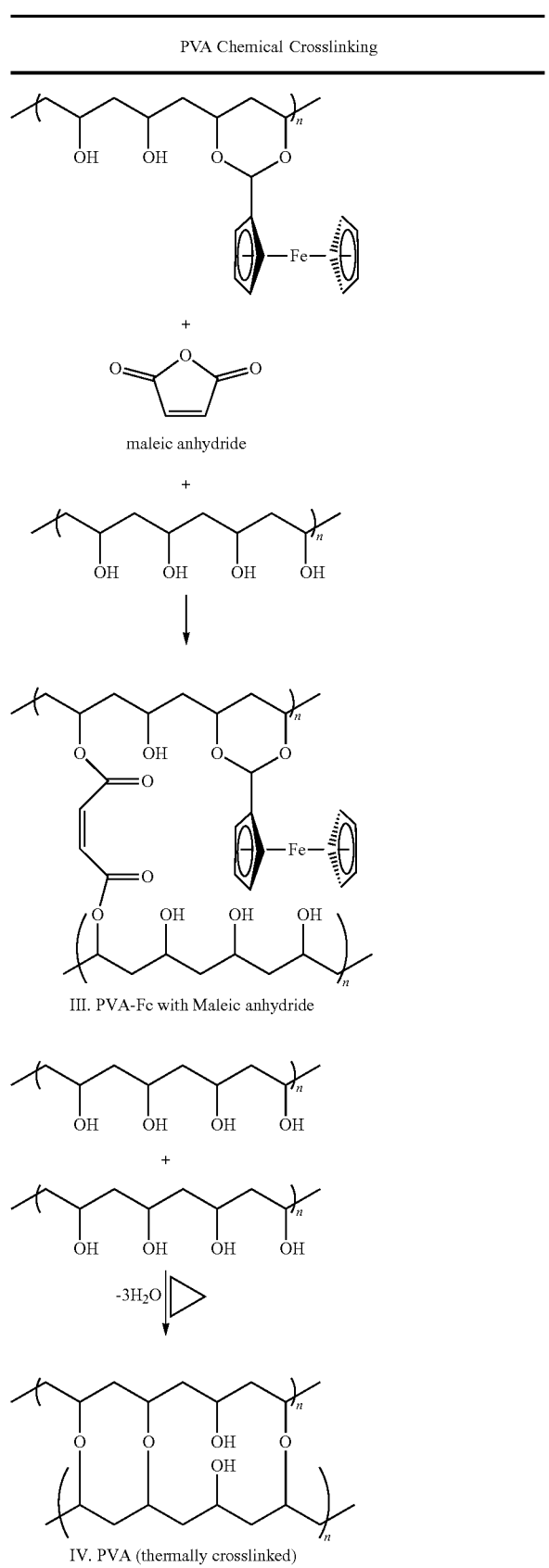

III. PVA-Fc with Maleic anhydride

IV. PVA (thermally crosslinked)

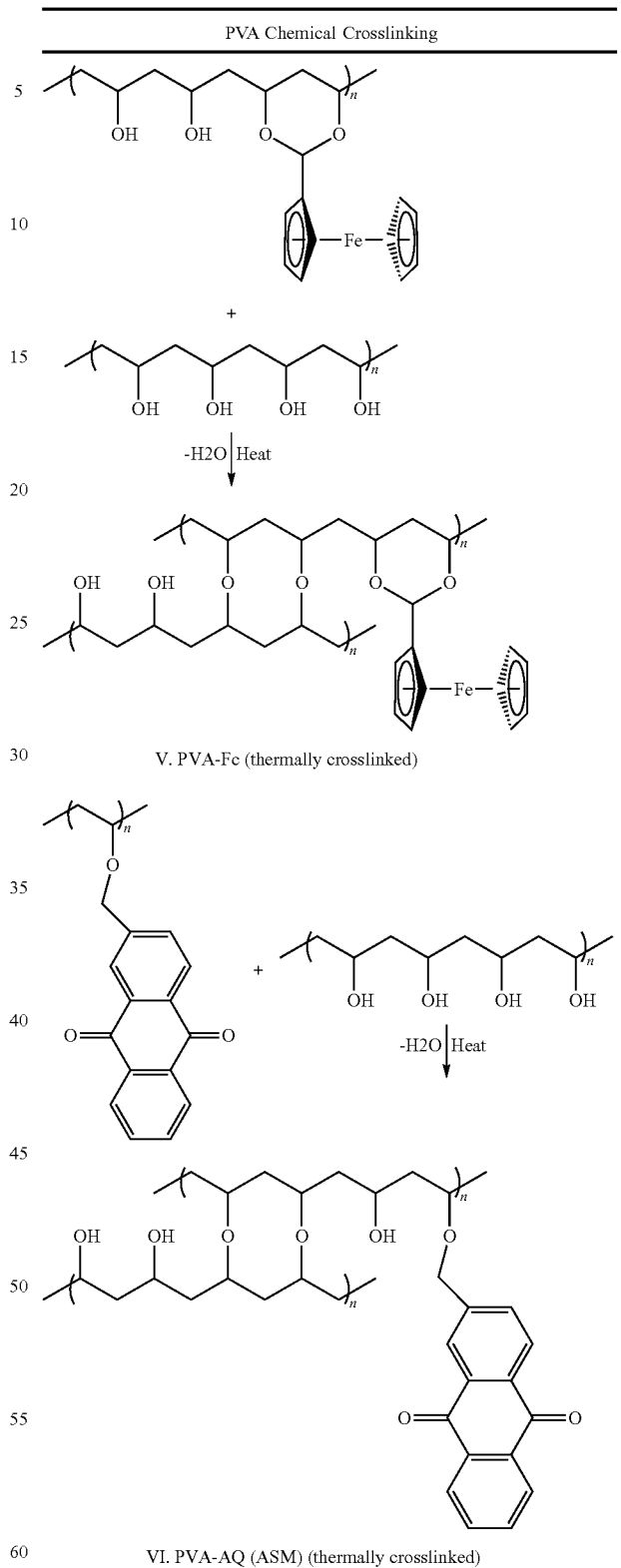

V. PVA-Fc (thermally crosslinked)

VI. PVA-AQ (ASM) (thermally crosslinked)

In one embodiment, glutaraldehyde crosslinker achieved a less swollen product than what is typically obtained by increasing the crystallinity of the hydrogel by heating, such as required with glycidyl methylacrylate crosslinker. In some instances, a selected chemical crosslinker requires high applied pressure to achieve effectiveness. For example, in some instances toluene diisocyanate and acrolien require high applied pressure for effectiveness. In other instances, certain copolymers require extreme high applied pressure, such as maleic anhydride/vinyl methyl ether compolymers. Thus, the high swelling tendencies of PVA copolymers, which may lead to dissolution, disintegration, or loss of mechanical strength for the polymer, may be overcome by crosslinking the co-monomers in accordance with various embodiments of the present invention. In some instances, crosslinking the PVA co-monomers results in the consumption of some of the OH groups responsible for the hydrophilicity of the polymer moiety. In some instances, the hydrophilic behavior of the polymer is intact after crosslinking the PVA monomers whereby the crosslinked polymer is mechanically robust and includes a tight network.

In some embodiments, polyvinylalcohol is functionalized with ferrocene and a linear polymer of the instant invention (e.g., a linear polymer which includes acetate groups, ferrocene and hydroxyl groups) that is either thermally crosslinked, chemically crosslinked, or crosslinked via radiation. For example, in one instance the crosslinkers are selected from the group consisting of maleic anhydride, maleic acid, glutaraldegyde, diisocyanate, divinyl ether, periodate, or any generic dialdehyde, as disclosed in http://ntrs.nasa.gov/archive/nasa/casi.ntrs.nasa.gov/19790012957.pdf, which disclosure is incorporated herein in its entirety. In some instances, PVA is functionalized with a ferrocene derivative having either a long side chain, or a shorter side chain and/or an electron withdrawing or electron donating group which is favorable in adjusting the peak potential to a more positive or more negative potential, depending upon the application. In some embodiments, certain ferrocene derivatives are selected because they are more robust and resistant to scan dependent decay, as disclosed in http://www.ncbi.nlm.nih.gov/pmc/articles/PMC2975373/table/T1/, which is incorporated herein in its entirety. The functional groups on ferrocene also change the peak potential, for instance, octamethyl ferrocene shows a peak at −80 mV instead of 220 mV.

Those of skill in the art will appreciate that the solid-state electrodes of the present invention can include AIMs, ASMs, or both. For example, in one embodiment vinylanthracene or 2-acrylamido-anthraquinone (shown below in Table 2) is incorporated into a hydrogel matrix to form an ASM hydrogel of the invention. Alternatively, both ASM- and AIM-vinyl monomers may be used as co-monomers in the single hydrogel material, wherein the hydrogel matrix material exhibits both analyte sensitive and analyte insensitive responses.

TABLE 2

Electrochemically active components

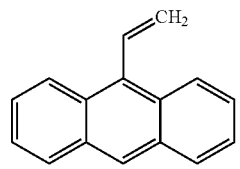

Vinylanthracene

TABLE 2-continued

Electrochemically active components 2-acrylamido-anthraquinone

In various embodiments of the electrodes, sensors, and devices of the invention, a polyacrylamide ferrocene conjugate and a polyacrylamide anthraquinone conjugate are used as an AIM and ASM respectively. Such embodiments include two linear polymers or a copolymer where both the ASM and AIM are incorporated in the polymer matrix as co-monomers resulting in a random copolymer of the desired composition. Thus, an ASM and an AIM may be integrated on a single electrode, wherein the single electrode generates two independent signals. In one embodiment, an ASM and an AIM are integrated onto a single electrode via a poly(vinyl alcohol) polymer, or a poly(vinyl alcohol) like polymer. In one embodiment, an ASM and an Aim are integrated onto a single electrode via an acrylamide polymer network. The present invention further includes an embodiment in which the ASM (e.g., WE) and AIM (e.g., IE) are on provided on separate substrates.

In some embodiments, an AIM such as a ferrocene derivative that is already in the form of an oligomer, polymer, or dendrimer, is used to prepare an AIM hydrogel in which the AIM is not covalently attached to the hydrogel but rather retained therein by physical entrapment. Effective physical entrapment requires that the effective network density of the hydrogel be sufficiently high to minimize diffusive loss of the ferrocene derivative (or other AIM) component. Monomeric AIMs are generally not suitable for physical entrapment as the high network density needed to retain them effectively is contrary to the requirement of a highly swollen hydrogel. Alternate hydrophilic scaffolds, including those based on sol-gel chemistry (see PCT Pub. No. 2012/018632, incorporated herein by reference), can be used to form IPNs to immobilize AIM polymers or AIM hydrogels (or corresponding materials with ASMs for preparation of WEs of the invention) with average molecular weights sufficiently high compared to the effective pore size of the scaffold to provide adequate immobilization.

For some solid-state electrodes of the present invention, ferrocene (or other AIM) polymers is blended into other polymer matrices to yield AIM polymers and AIM hydrogels of the invention. In some embodiments, such matrices are selected to impart certain optimized attributes, such as thermal or chemical resistance, that exceed the performance envelop of non-optimized hydrogels. Other materials which may be used to impart optimized attributes include polyvinylidenefluoride (PVDF), epoxy, electropolymerized polypyrrole, and various conductive ink formulations. These and other polymers may be employed in various solid-state sensor embodiments of the present invention to meet the mechanical, dielectric, or physicochemical requirements of application-specific sensors assemblies and/or devices.

Electrode Arrangement

The invention provides robust electrodes without covalent attachment of the AIM to the substrate or the ASM to its substrate, which may be the same or different. In some electrodes of the invention, the AIM hydrogel is secured to the substrate surface by non-covalent means. The invention provides substrates that enhance such attachment, having the appropriate level of surface texture, porosity, and/or three-dimensional tortuosity to ensure secure immobilization. These features can improve attachment and/or containment of the AIM hydrogel (or ASM hydrogel) without affecting the AIM's interaction with the analyte, in part benefitting from the highly permeable nature of the swollen hydrogel. They also provide protection against physical damage associated with contact, abrasion, or detachment that might otherwise result from repeated swelling and shrinking of the AIM hydrogel, compared with the same material deposited on a smooth surface such as glassy carbon, or other metallic and non-metallic surfaces. In effect, the mechanical properties of the textured or porous substrate overcome the inherent fragility of AIM hydrogel to deliver high structural integrity.

Any conductive substrate can be used as an electrode for the support, immobilization, and protection of AIM polymers and AIM hydrogels (and ASM polymers and ASM hydrogels) of the invention. These can include carbon allotropes such as carbon fiber, porous graphite, macroporous carbon, mesoporous carbon, microporous carbon, nanoporous carbon, carbon nanofibers (made by carbon-coating on materials such as nanoporous alumina) and their composites; and nanotubes and their composite. Metals can include nanoporous gold, platinum, and silver. Screen-printed electrodes can have a variety of surface coatings with desired roughness including mesoporous carbon, carbon nanofibers, carbon nanotubes, graphene, or carbon ink imprinted with micro- or nano-scale features such as channels or pores. Porous conductive substrates benefit further from very short signal pathways, thereby increasing signal capture efficiency.

Certain conductive polymers can be used as an electrode substrate and coated with AIM hydrogel. Engineering polymer composites that contain sufficient quantities of carbon allotrope or metal particles to render them conductive can be used as supports for the AIM hydrogel. Suitable polymers for such composites include epoxy, polysulfone, polyethersulfone, polyphenylenesulfide, polypyrrole, polyvinylidenefluoride, other fluoropolymers or copolymers, and various vinyl polymers such as PVC, polystyrene, polymethylmethacrylate, and their derivatives and copolymers, cellulosic polymers, and silicone polymers.

Electrodes of this invention can be made using rigid substrates such as various carbon composites, or on flexible conductive substrates (e.g. woven or nonwoven carbon fabric), or a nonconductive support film such as polyester, polyimide, polyolefin, etc. that has been rendered conductive with a conductive coating (such as carbon ink, indium tin oxide, silver, etc.). The materials of the present invention may be formed in various geometric patterns, which may include arrangements whereby the CE and PRE are arranged in close proximity. For example, the electrodes may be arranged as concentric rings, segments, and arrays, as shown in FIGS. 6A and 6B. Conductive coatings and electrodes derived therefrom allow sensors to be built in a wide range of form factors and dimensions.

Various embodiments of the present invention comprise a sensor assembly, device, or module having two or more electrodes that are uniquely and purposefully arranged to optimize the performance thereof. In some embodiments, the arrangement of the plurality of sensors is selected to achieve a desired proximity of two or more compatible or companion electrodes. In some embodiments, the arrangement of the plurality of sensors is selected to achieve a desired ratio of RASAs between two or more compatible or companion electrodes. In some embodiments, the arrangement of the plurality of electrodes is selected to minimize an insertion depth for the sensor assembly, device or module. Further, in some embodiments the arrangement of the plurality of sensors is selected to accommodate a specific application or product platform device.

In some embodiments, a sensor assembly, device, or module comprises a plurality of electrodes arranged as concentric rings, partitioned segments, or arrays, as shown in FIGS. 6A and 6B. With reference to FIG. 6A, some embodiments of the present invention comprise a conductive substrate material having a segmented sensor arrangement comprising an ASM-containing WE 60, an AIM-containing IE 62, a PRE 64, and a CE 66, wherein each electrode is surrounded by nonconductive material 68 to separate and insulate the electrodes from one another. The electrodes are further connected to electronic circuitry of the sensor device for square-wave voltage operation.

In some instances, sensor materials or composites are formed into micro-hemispheres with characteristic radii on the order of 25 micrometers or less. Sensors of these dimensions generate very low signals, but their reduced double layer capacitance also shortens the response time. (see J. Wang, *Analytical Chemistry*, $3^{rd}$ ed., 2006, John Wiley). Sensor arrays can be constructed for use in miniaturized or microelectrodes with viable signal levels for practical applications. In some instances, an AIM-containing electrode and an ASM-containing electrode are built into alternating microquadrants to provide a network of ASM and AIM sensors. In one embodiment, this plurality in the network of ASM and AIM sensors increases the rate of monitoring an analyte, as may be required by an application. For example, ASM and AIM sensors configured in alternating microquadrants could be configured to operate using the same or similar scan parameters, but in different scan windows. In one embodiment, the ASM and AIM sensors are scanned alternatively with same or different scan parameters. In one embodiment, the ASM and AIM sensors are scanned concomitantly.

With reference to FIG. 6B, some embodiments of the present invention comprise a conductive substrate material having a concentric sensor arrangement comprising an ASM-containing WE 60, an AIM-containing IE 62, a PRE 64, and a CE 66, wherein each segmented sensor is surrounded by nonconductive material 68 to separate and insulate the electrodes from one another. The electrodes are further connected to electronic circuitry of the sensor device for square-wave voltage operation.

Figure 7B:
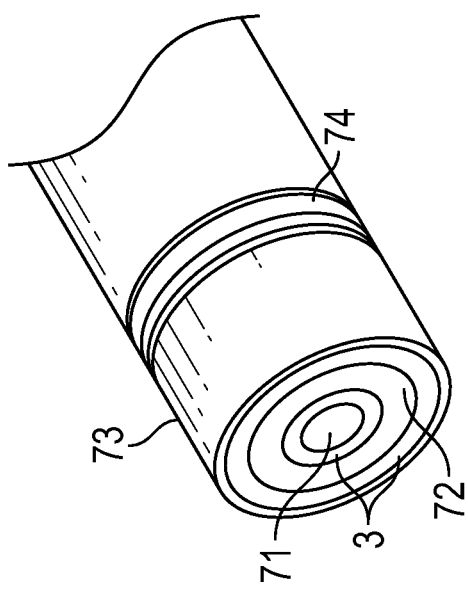
FIGS. 7A and 7B show perspective views of a hybrid sensor probe assembly in accordance with a representative embodiment of the present invention.
Figure 7A:
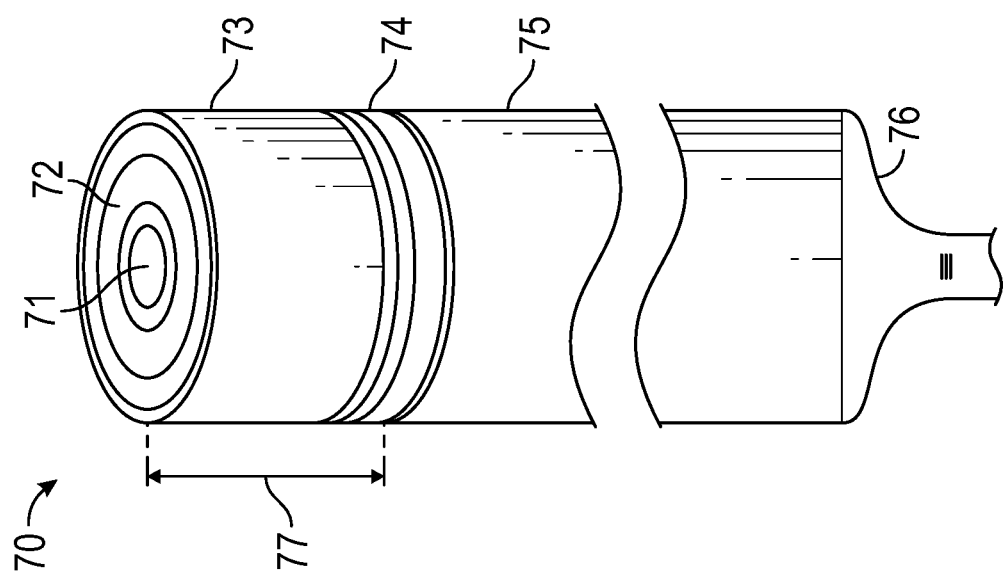

Some embodiments of the present invention further comprise a hybrid sensor probe assembly 70, as shown in FIGS. 7A and 7B. Sensor assembly 70 comprises a PRE 71 at the axial center of the assembly. An annular WE 72 surrounds PRE 71 and further comprises an insulating material or space interposed between WE 72 and PRE 71. Sensor assembly 70 further comprises a CE 73 which surrounds WE 72 and provides an outer tip surface for assembly 70. Sensor assembly 70 further comprises an insulating material 3, space or epoxy moat interposed between WE 72 and CE 73, and further between WE 72 and PRE 71. Assembly 70 further comprises an insulating material, such as a rubber grommet 74, between CE 73 and the handle 75 of assembly 70. Further still, sensor assembly 70 comprises electrical circuitry (not shown) which operably connects the various electrodes and sensor components to at least one of an on-board printed circuit board (not shown), and a wire harness 76 that is coupled to an external printed circuit board (not shown).

Some electrode configurations and/or sensor assemblies of the present invention further comprise a minimum insertion depth. In some embodiments, the minimum insertion depth is determined by a position of one or more electrode, wherein the minimum insertion depth causes one or more electrode to be completely immersed in an analyte solution. For example, in some instances CE 73 comprises a minimum insertion depth 77 which is approximately equal to a height of CE 73. In some embodiments, the minimum insertion depth is determined by a minimum percentage of the surface area of one or more electrodes that is required to be immersed in an analyte solution in order to obtain an optimal output signal in a desired range for the sensor assembly/device. For example, in one embodiment a minimum insertion depth or surface area is selected to provide a signal output in the milliamp range. In one embodiment, a minimum insertion depth corresponds to immersion of a minimum electrode surface area of less than 1%, from 1-5%, from 5-10%, from 10-20%, from 20-30%, from 30-40%, from 40-50%, from 50-60%, from 60-70%, fro 70-80%, from 80-90%, or from 90-100%. In one embodiment, a minimum insertion depth corresponds to immersion of a minimum electrode surface area of 50%. In one embodiment, a minimum insertion depth is determined based on a minimum collective surface area of all electrode of a sensor assembly. In one embodiment, each electrode of a sensor assembly comprises a minimum electrode surface area, wherein the minimum insertion depth is determined by the depth of insertion wherein the minimum electrode surface area of each electrode is immersed. In some embodiments, the position of one or more electrodes of a sensor assembly is arranged, and/or the properties of one or more electrodes of the sensor assembly is optimized, to minimize the minimum insertion depth of the sensor assembly.

Figure 8A:
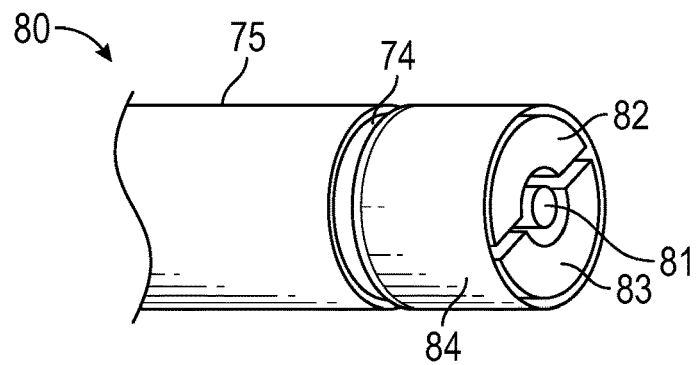
FIG. 8A is a perspective view of a sensor probe assembly comprising hemispheric cross-section sensors in accordance with a representative embodiment of the present invention.
Figure 8B:
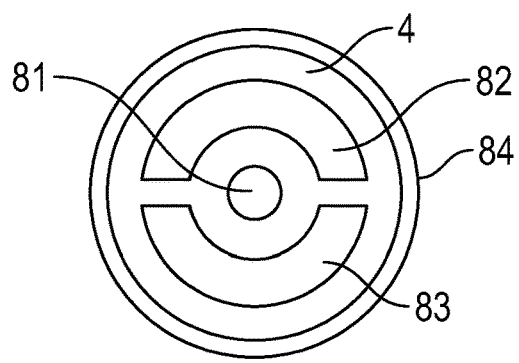
FIG. 8B is a plan top view of a sensor probe assembly comprising hemispheric cross-section sensors in accordance with a representative embodiment of the present invention.

Some embodiments of the present invention further comprise an analyte sensing device 80 which comprises a sensor tip having an ASM-containing WE 82, an AIM-containing IE 83, and a RE (or PRE) 81, as shown in FIGS. 8A and 8B. In this embodiment, WE 82 and IE 83 each comprise a hemispheric cross-section and are positioned inside of CE 84 to surround RE 81. Assembly 80 further comprises an insulating material or space between the various surfaces of RE 81, WE 82, IE 83, and CE 84. A rubber grommet or other insulating material 74 is further interposed between CE 84 and handle 75, as discussed above.

Figure 9A:
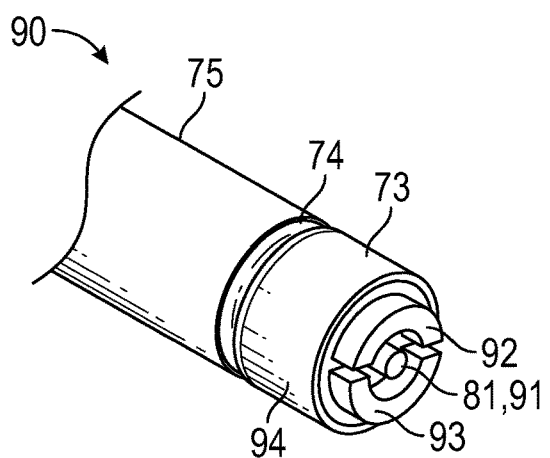
FIG. 9A is a perspective view of a sensor probe assembly configured to increase the sensor surface areas in accordance with a representative embodiment of the present invention.
Figure 9B:
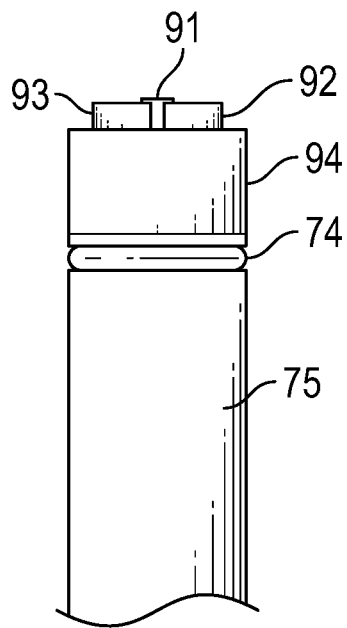
FIG. 9B is a plan side view of the sensor probe assembly shown in FIG. 9A.

In some embodiments, the analyte sensing device comprises various features to increase the RASA of one or more of the device's electrodes. For example, in some instances an analyte sensing device comprises a probe assembly 90 comprising a sensor tip having an ASM-containing WE 92, an AIM-containing IE 93, and a RE (or PRE) 91, wherein a portion of the RASA of each electrode extends distally beyond the end surface of a CE 94, as shown in FIGS. 9A and 9B. In this embodiment, WE 92 and IE 93 each comprise a hemispheric cross-section and are positioned inside of CE 94 to surround RE 91. Assembly 90 further comprises an insulating material or space between the various surfaces of RE 91, WE 92, IE 93, and CE 94.

Figure 10A:
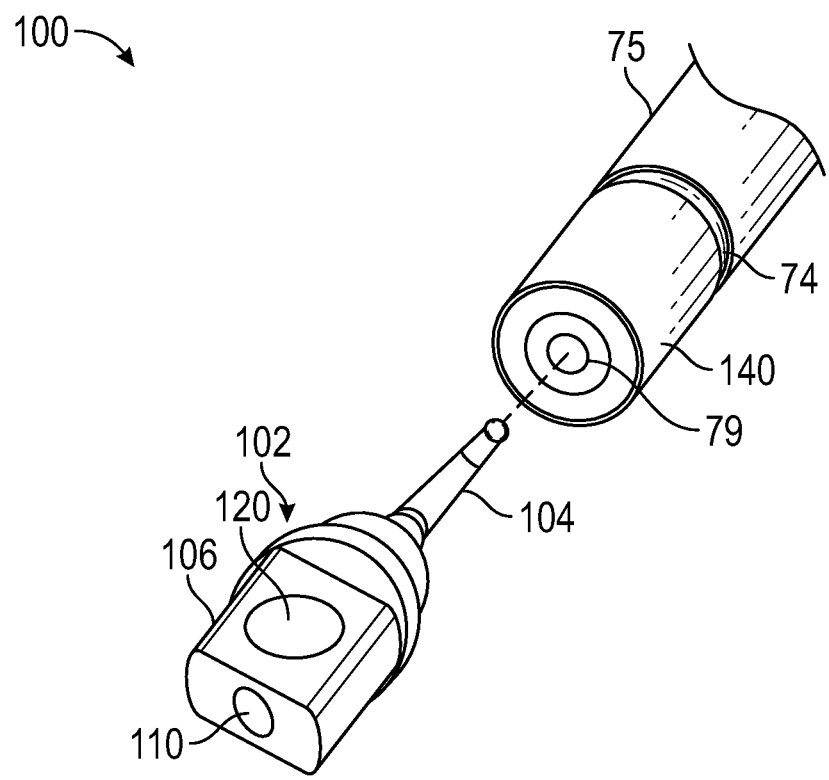
FIGS. 10A-10F comprise various views of a probe assembly having a sensor tip comprising sensors arranged to provide increased sensor surface areas in accordance with representative embodiments of the present invention.

Referring now to FIGS. 10A-10F, some embodiments of the present invention further comprise a probe assembly 100 having a sensor tip 102 having electrodes arranged to optimize the RASA of each electrode of the sensor tip. In some instances, sensor tip 102 comprises optimized, flattened surfaces which provide a paddle-like extension 106. In some embodiments, extension 106 comprises opposing mounting surfaces having surface areas optimized to maximize the RASA of electrodes coupled thereto. In some instances, compatible or companion electrodes are mounted to the opposing, flattened surfaces of extension 106. For example, in one embodiment an ASM-containing WE 120 is mounted to a top surface of extension 106, and an AIM-containing IE 130 is mounted to a bottom surface of extension 106. Probe assembly 100 further comprises a cylindrically-shaped CE 140 which is positioned in proximity to extension 106, and which comprises an exposed surface area defining an outer perimeter of the probe portion of assembly 100. CE 140 is insulated from WE 120, IE 130, and the remaining non-electrode materials of sensor tip 102 via a rubber grommet or O-ring 74. Further still, probe assembly 100 comprises a RE 110 comprising an end or distal surface of extension 106. RE 110, WE 120, and IE 130 are insulated from one another via the non-electrode materials of extension 106. In some embodiments, assembly 100 may further include a PRE (not shown) embedded beneath CE 140. Probe assembly 100 may further comprise circuitry and an electrical contact 104 to permit operable connectivity to probe handle 75 and/or CE 140, as shown in FIG. 10A.

In some embodiments, sensor tip 102 is permanently coupled to handle 75 and/or CE 140, wherein sensor tip 102 comprises an integral component of probe assembly 100. In other embodiments, sensor tip 102 comprises a replaceable sensor module that is removably coupled to sensor tip 102 via one or more electrical connections. For example, in one embodiment a distal end of handle 75 comprises an electric socket 79 for selectively receiving a compatible electric contact 104 of sensor tip 102. In one embodiment, electric socket 79 comprises a female jack and electrical contact 104 comprises a male plug. In one embodiment, sensor tip 102 is operably and selectively coupled to the distal end of handle 75 via any compatible electric connection.

Figure 10B:
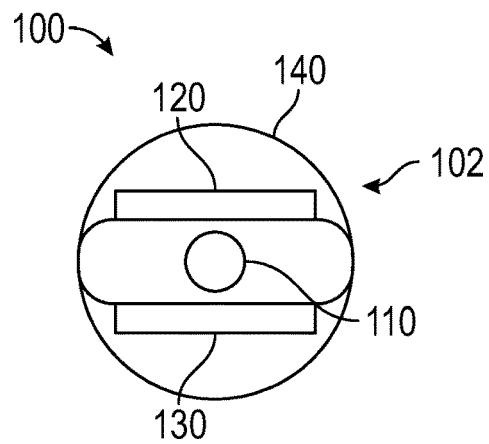
Figure 10C:
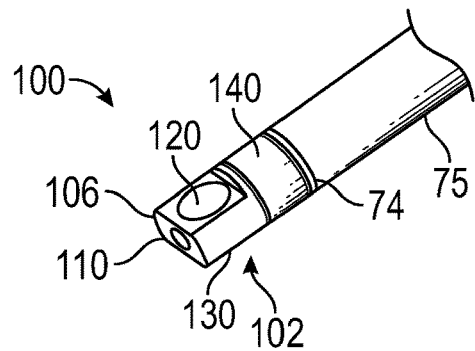
Figure 10D:
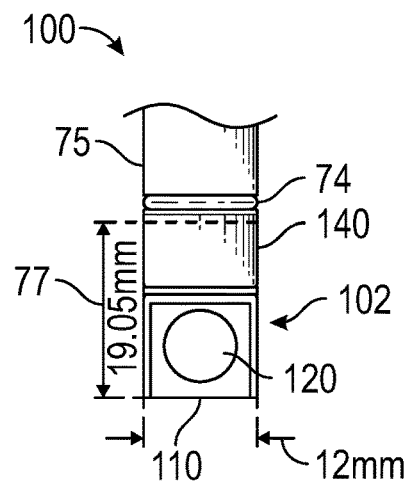
Figures 10E, 10F:
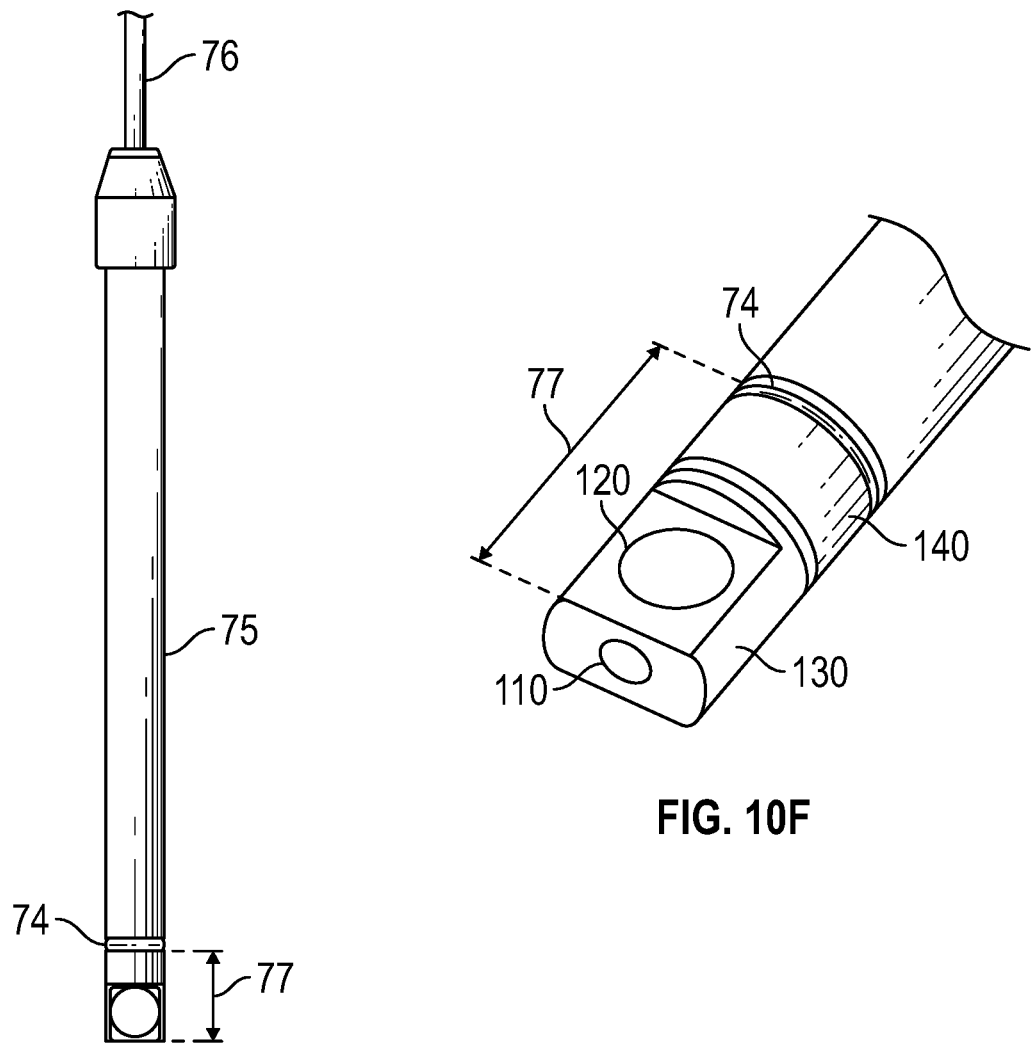

In some instances, ASM-containing WE 120 and AIM-containing IE 130 comprises a carbon fiber epoxy material (Dragon Plate or ACP Composites) and exposed diameter selected to maximally fill the top and bottom surfaces, respectively. In some embodiments, WE 120 and IE 130 are flush fitted into their respective surfaces, as shown in FIGS. 10A, and 10C-10F. In one embodiment, WE 120 and IE 130 are inset or surface mounted onto their respective surfaces such that a portion of each electrode extends outwardly from the mounting surface, thus increasing the exposed RASA of the electrodes, as shown in FIG. 10B.

In one embodiment, CE 140 comprises a 316 grade stainless steel tube having a height 77 of approximately 19.69 mm, wherein height 970 is equal to, or approximately equal to a minimum insertion depth for probe assembly 100. Probe handle 75 further comprises a 304 grade stainless steel tube that is insulated from CE 140 via rubber grommet or O-ring 74. In some instances, probe handle 75, sensor tip 102, CE 140, and O-ring 74 comprises a combined height of approximately 164.41 mm.

Figure 11A:
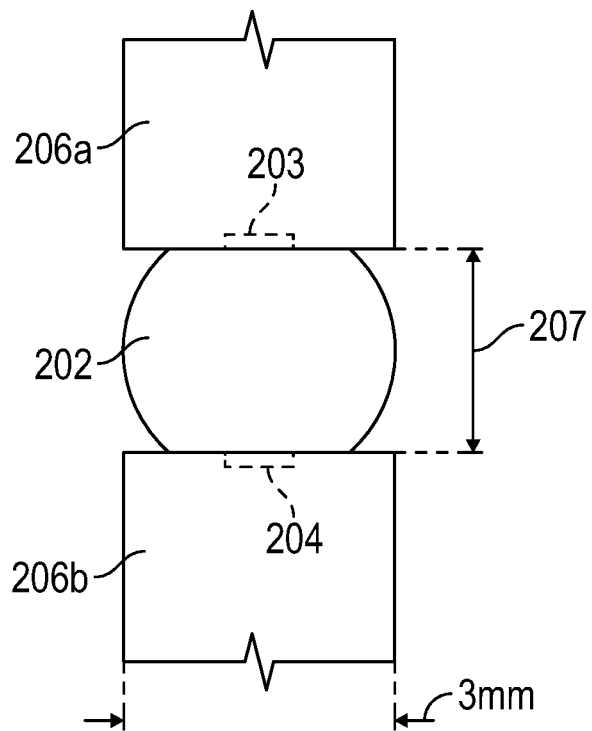
FIGS. 11A and 11B show a side view and a top plan view of a sensor comprising two halves which are used together to detect an analyte in accordance with a representative embodiment of the present invention.
Figure 11B:
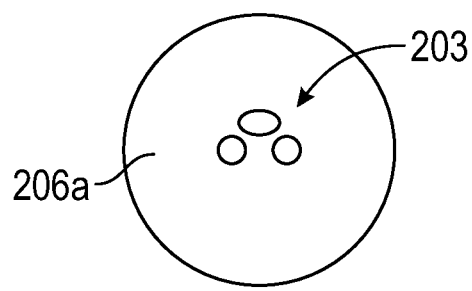
Figure 11B:
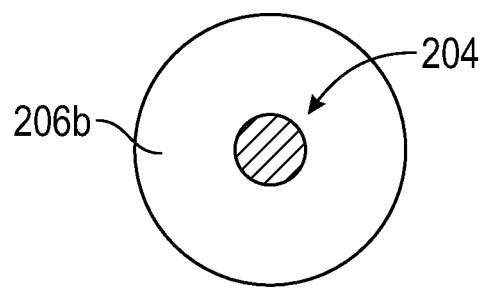

Referring now to FIGS. 11A and 11B, some embodiments of the present invention further comprise a sensor configuration whereby a first sensor group 203 comprising one or more sensors is arranged on a first substrate 206a, and a second sensor group 204 comprising one or more sensors is arranged on a second substrate 206b, wherein the first and second sensor groups 203 and 204 of the first and second substrates 206a and 206b are arranged contact a portion of a single analyte sample 202. In one embodiment, the first and second sensor groups are located in areas on the order of several square millimeters or several square micrometers.

The proximity of the sensor groups ensures that the electrodes will be in contact with the sample at the same time. A circuit between the first and second substrates 206a and 206b is completed when an analyte droplet bridges a gap between the two sensor groups 203 and 204. There is current flow only when a sample droplet bridges the two sensor groups of the sensor assembly.

Figure 11C:
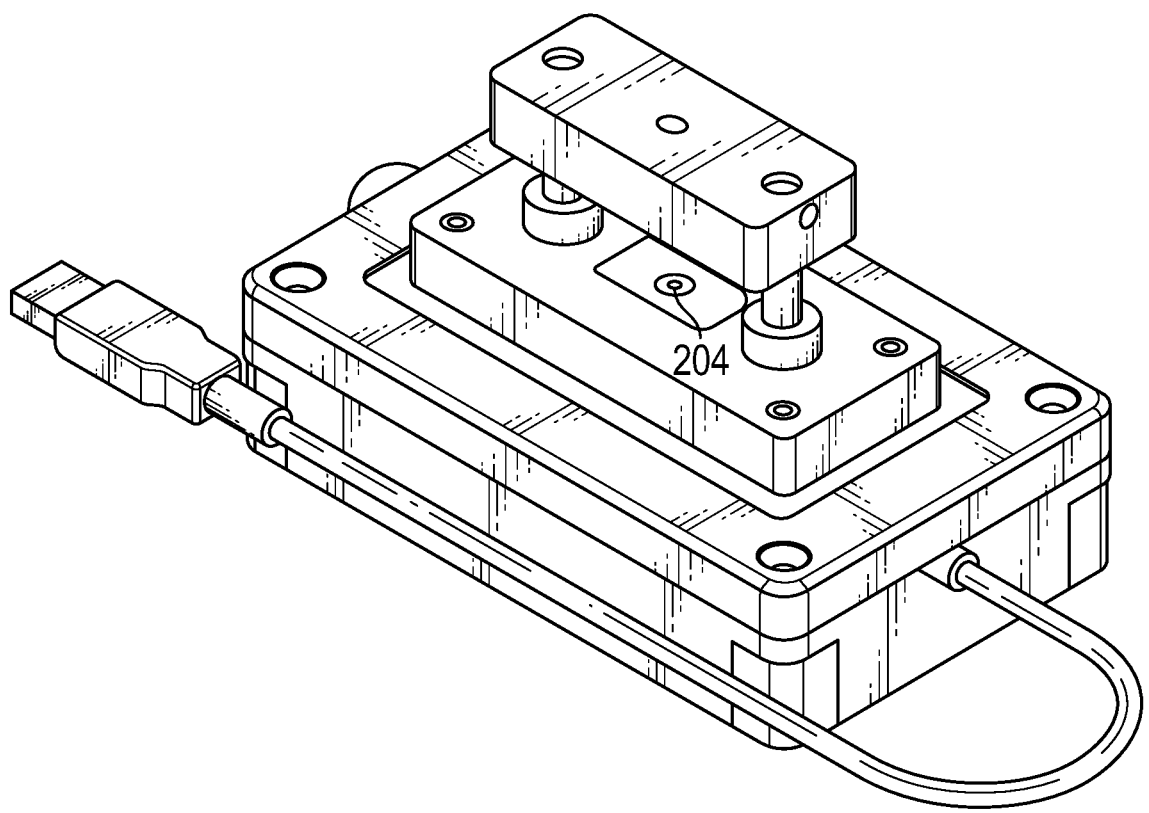
FIG. 11C shows perspective, top and side views of a droplet sensor in accordance with a representative embodiment of the present invention.

In some instances, first sensor group 203 comprises a WE, a IE, and a PRE, while second sensor group 204 comprises a CE. One having skill in the art will appreciate other possible sensor arrangements, as discussed herein and in accordance with the spirit of the teachings herein. In one embodiment, first and second substrates 206a and 206b are positioned opposite one another such that first and second sensor groups 203 and 204 are oppositely positioned and comprise a space or gap 207 between the sensor groups 203 and 204 configured to receive analyte sample 202. In one embodiment, analyte sample 202 is a droplet of an analyte solution, wherein gap 207 is configured to retain sample 202 via capillary forces. In one embodiment, the analyte sample 202 comprises a volume of approximately a milliliter, approximately a microliter, approximately a nanoliter, or approximately a picoliter. A non-limiting example of a droplet sensor device is shown in FIG. 11C.

Product Platform Devices

Various embodiments of the present invention may be deployed widely across multiple platforms. For example, the sensor assemblies and/or modules of the present invention may be incorporated in a variety of housings, containers, electronic modules for subsystem integration, sample plates, sample tubes, cell culture bags, wave bags, biobags, reactors for pharmaceutical labs, packaging and monitoring of materials, such as food or other perishables, beverage, dairy, personal care, and biological materials and products, high throughput applications, and the like. In some instances, the sensor assemblies of the present invention are adapted for use in a variety of markets or industries, including but not limited to institutional and/or educational research and development, life sciences, biopharma, food and beverage, dairy, pharmaceuticals, nutraceuticals, cosmetics, product packaging, agriculture, hydroponics, soil, environmental, medical devices, oil and gas, and the like. In some instances, an industry, market or product requires a customized form factor, package, or development pathway to accommodate implementation of the sensor assemblies of the present invention into their specific application. Accordingly, the sensor assemblies of the instant invention may be modified as needed to accommodate a specific application. For example, in some instances the size of a sensor assembly may be reduced or increased, as desired. In other instance, a sensor assembly may comprise a two- or three-dimensional structure that is compatible for use in a desired application. In other instances, a sensor assembly may comprise one or more optimized solid-state electrodes.

Some embodiments of the present invention comprise one or more product platform devices comprising one or more electrodes having a RASA in accordance with the present teaching. Product platform devices may comprise any component, apparatus, surface, or structure for use in holding and/or analyzing an analyte solution or material, wherein the component, apparatus, surface, or structure further comprises one or more electrodes having a RASA in accordance with the present invention. Non-limiting examples of product platform devices are shown and described below.

Sensor Tip Module

As discussed previously in connection with FIGS. 10A-10F, various embodiments of the invention provide a sensor module comprising a sensor tip for use with a handheld sensor probe assembly. In some embodiments, the sensor tip comprises a plurality of optimized electrodes that may be gamma sterilized for repeated use. In other embodiments, the sensor tip module comprises a replaceable, disposable and/or single-use sensor module having one or more optimized features. In some instances, the sensor tip comprises one or more solid-state electrodes, and in a specific embodiment comprises a solid-state RE. In one embodiment, the sensor tip module is miniaturized and applied to a distal tip of a catheter for surgical applications, such as end point detection in a continuous flow cell.

Health Diagnostics

As discussed previously in connection with FIGS. 11A-11C, some embodiments of the present invention comprise a health diagnostics sensor assembly that may be used to measure an analyte in a biological fluid, such as blood, urine, or saliva. In one embodiment, a health diagnostics sensor assembly comprises two opposing halves, each half comprising opposing sensor groups having one or more compatible or companion electrodes. A gap between the opposing sensor groups is configured to collect and retain a biological fluid sample, such as by capillary forces. The gap may be configured to retain a small volume of fluid, such as a milliliter, a microliter, a nanoliter, or a picoliter of fluid. In some instances, the opposing sensor groups of the health diagnostic sensor assembly are placed in a continuous flow system, such that a fluid contacts the opposing groups to measure an analyte in the fluid.

Handheld pH Probe Sensor Assembly

As discussed previously in connection with FIGS. 10A-10F, some embodiments of the present invention comprise a handheld pH probe sensor assembly having a sensor tip comprising one or more optimized solid-state electrodes, wherein the sensor tip may be manually inserted in an analyte-containing solution. In one embodiment, a sensor tip of the probe assembly comprises a diameter of 12 mm, wherein one or more of the optimized solid-state electrodes are located on the distal, planar surface of the sensor tip. In one embodiment, a CE of the probe assembly is located on the distal, planar surface of the sensor tip. In another embodiment, a CE of the probe assembly comprises a collar or circular trace surrounding the remaining electrodes of the sensor tip. Handheld pH probe assemblies that are compatible for use with the optimized solid-state electrodes of the present invention are disclosed in WO/2010/104962, WO/2010/111531, WO/2010/146152, WO/2012/018632, WO/2013/112767, WO/2013/134582, WO/2014/106066, and WO/2015/191924, each of which is incorporated herein by reference.

Sample Plate

Figure 12:
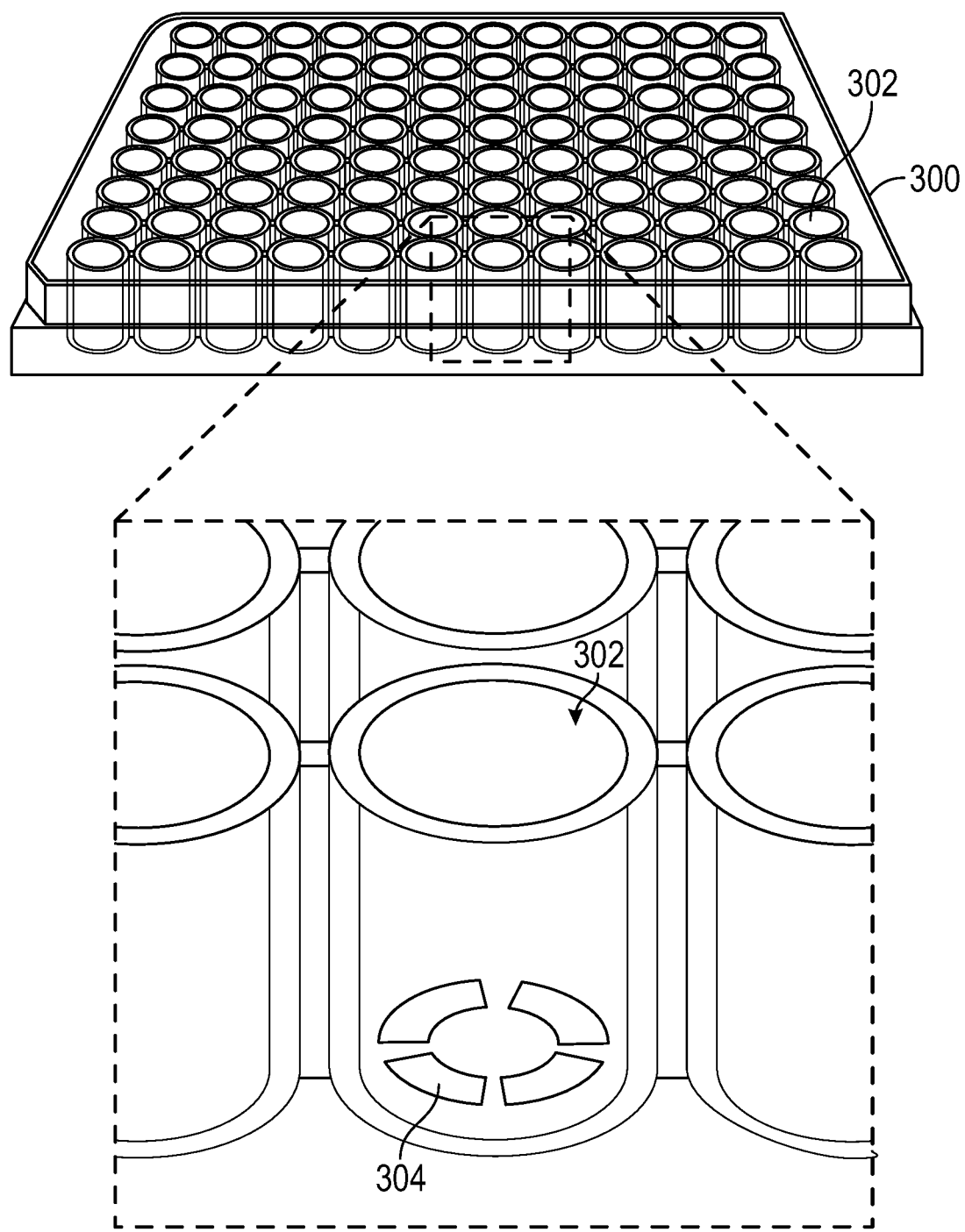
FIG. 12 shows examples of sensors of the invention integrated into the internal surface of a sample cavity. Not shown are electrical connections to each electrode. These connections can be effected, in accordance with the invention, by masked printed conductive traces, through-hole plating, and similar techniques. One or more of the electrodes can also be situated on the vertical internal perimeter surface of the sample cavity, thereby leaving at least a portion of the bottom of the sample cavity transparent and so available for optical measurements.

Another embodiment provided by the invention is a multiwell or microwell plate 300 in which there is an addressable sensor in the bottom and/or internal wall of every well 302, wherein the sensor comprises one or more optimized solid-state electrodes 304 have a RASA, as shown in FIG. 12. In some embodiments, the configuration of the electrodes is similar to the sensor tip of the handheld probe assembly discussed above. The primary difference between these sensors is the size or surface areas of the individual electrodes, as well as electronic interface. In the case of a multiwell plate, the electrical connections to each electrode can be achieved through holes to the backside of the plate or by means of conductive traces. These connections are common in multiwell plate sensors for monitoring conductivity. In a typical configuration, a 96-well plate will contain 50-200 microliters of solution per well. The electrode surfaces at the bottom of each well will be on the order of 1-2 square millimeters; the diameter of the wells is about 1 cm. In an alternate embodiment, electrodes may be incorporated into multiwell plates such that the analyte will contact all sensing elements to enable measurement. In certain embodiments, one or more electrodes are located on the walls of the sample cavity, leaving at least a portion if not all of the bottom transparent for optical analysis. Alternatively, printed electrodes located on a flexible film are particularly suited as components in flexible containers, tube sets, and other components for bioprocessing (including single-use or disposable components), as discussed herein.

Product Development Kit

Figure 13A:
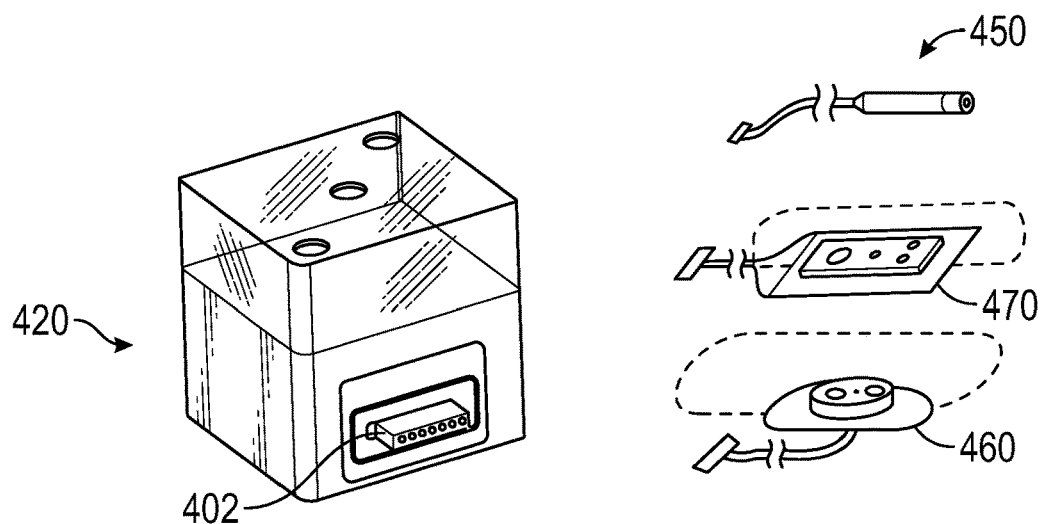
FIGS. 13A-13C show perspective views of various product platform devices and sensor interface devices in accordance with representative embodiments of the present invention.
Figure 13B:
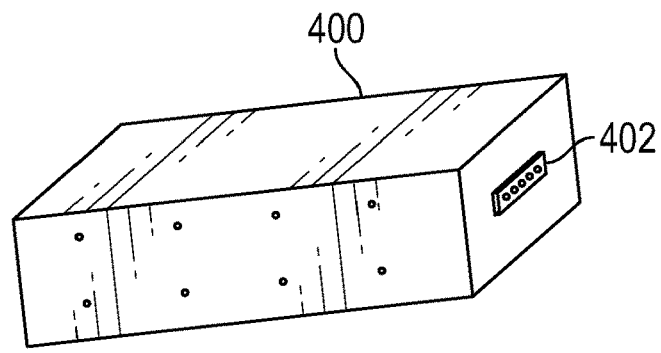
Figure 13C:
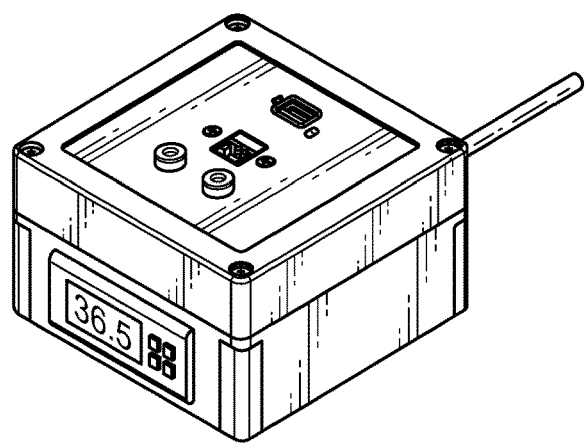

Referring now to FIGS. 13A-13C, some embodiments of the present invention comprise a product development kit 400 which may be used with various sensor assemblies or devices 450, 460, and 470. In some embodiments, product development kit 400 is use with a sensor assembly or device comprising at least one electrode having a RASA. In some embodiments, development kit 400 comprises system electronics that are useful in receiving and compiling electrical signals from various sensor assemblies or devices of the present invention. In one embodiment, development kit 400 comprises software and hardware to enable square-wave voltage analysis for electrical signals received from one or more sensor assemblies or devices. In some embodiments, development kit 400 comprises at least one I/O port 402 that is configured to operably receive and connect to one or more sensor assembly devices 450, 460 and/or 470 as part of a development testing protocol. Thus, development kit 400 may be used as an integral tool in developing platform specific applications utilizing one or more sensor assembly devices of the instant invention. In some instances, development kit 400 is used in combination with an interactive sensor management system 420 which comprises a product development kit 400 and a graphical user interface, as discussed below.

In one embodiment, development kit 400 is used in combination with sensor probe assembly 450. In some embodiments, a sensor assembly comprises a device designed for integrated use in various containers and packaging materials intended to store an analyte-containing material or solution, such as sensor assembly 460. In some embodiments, development kit 400 is further used in combination with a 2-dimensional universal sensor assembly 470 which may be incorporated into a variety of products or sensing devices, as described below.

Sensor Assembly Storage Containers

Some embodiments of the present invention further comprise sensor assemblies or devices comprising storage containers having one or more surfaces into, or onto, which is incorporated one or more solid-state electrodes having a RASA. In some instances, the one or more solid-state electrodes are incorporated into a single-use container, such as a cell culture bag, a reaction vessel, a sample plate, a sample vial, packaging for transporting and selling food items, and the like. In other embodiment, the solid-state sensor electrodes are incorporated into a multi-use, or reusable container.

In some embodiments, a storage container comprises a hybrid sensor assembly having a planar design and configured with one or more optimized solid-state electrodes for detecting a wide range of analytes. In one embodiment, a hybrid sensor assembly is provides that is non-contaminating in sensitive environments. In one instance, the hybrid sensor assembly may be sterilized, such as by gamma radiation. The hybrid sensor assembly may further be structurally flexible and adaptable for use with a variety of analyte-containing materials or products, such as food and beverage items, biological samples, chemicals, and the like.

Sample Docking Station

Referring now to FIGS. 14A-14D, some embodiments of the present invention comprise a sensor assembly docking station 500 that is configured for use with various storage containers having one or more solid-state electrodes embedded within or otherwise located on a portion of the container, wherein the one or more solid-state electrodes operably connects with the sensor docking station 500 when the container is placed thereon. In some embodiments, docking station 500 comprises a sensor reader 510 having a plurality of contacts 520 that are positioned for alignment with corresponding electrode contacts located on an outer surface of storage containers for use with docking station 500. Contacts 520 are electrically connected to a wire harness 502 having an electrical connector 504 that may be coupled to a compatible reader, such as product development kit 400. Docking station 500 may comprise any size, shape and/or surface configuration for compatible use with a desired container. In one embodiment, a sample docking station is configured to receive a storage container configured to transport and/or store processed food, vegetables and/or fruits, wherein the sample docking station measures and reports a status or change in a pH of the contents. In one embodiment, the pH status of the contents indicates a freshness or useful shelf life of a product stored in the container.

Reaction Vessel

Figure 14A:
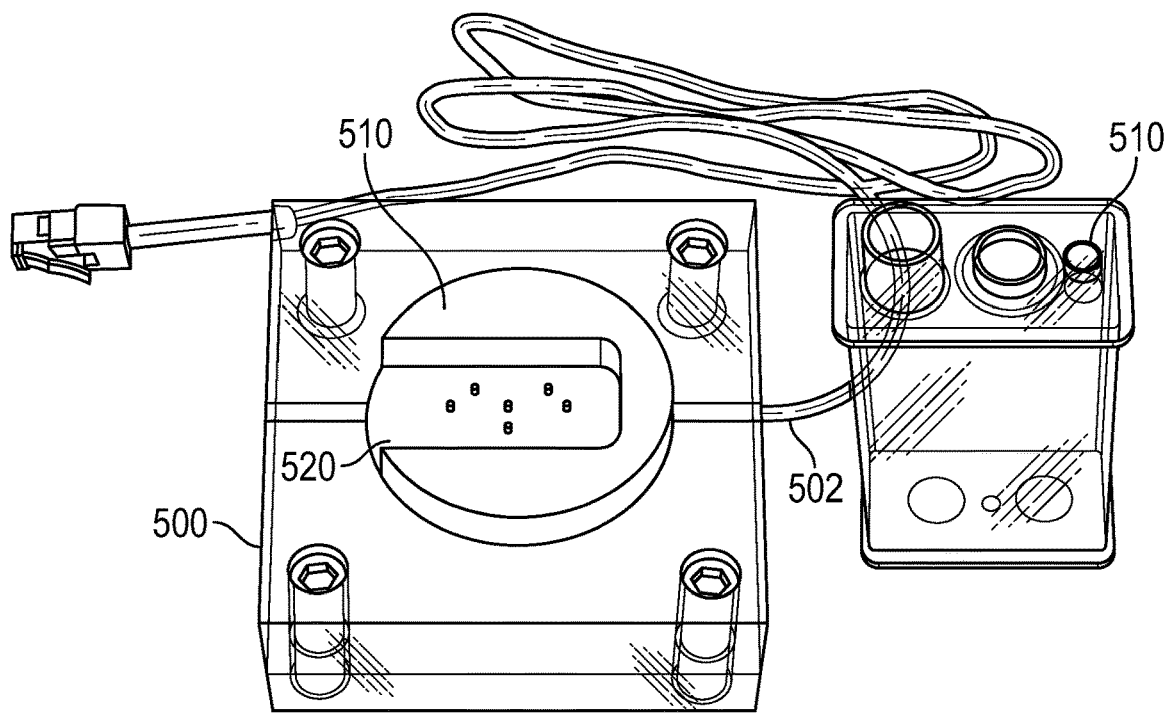
FIGS. 14A-14D show perspective views of various sensor docking stations and sample vessels in accordance with representative embodiments of the present invention.
Figure 14B:
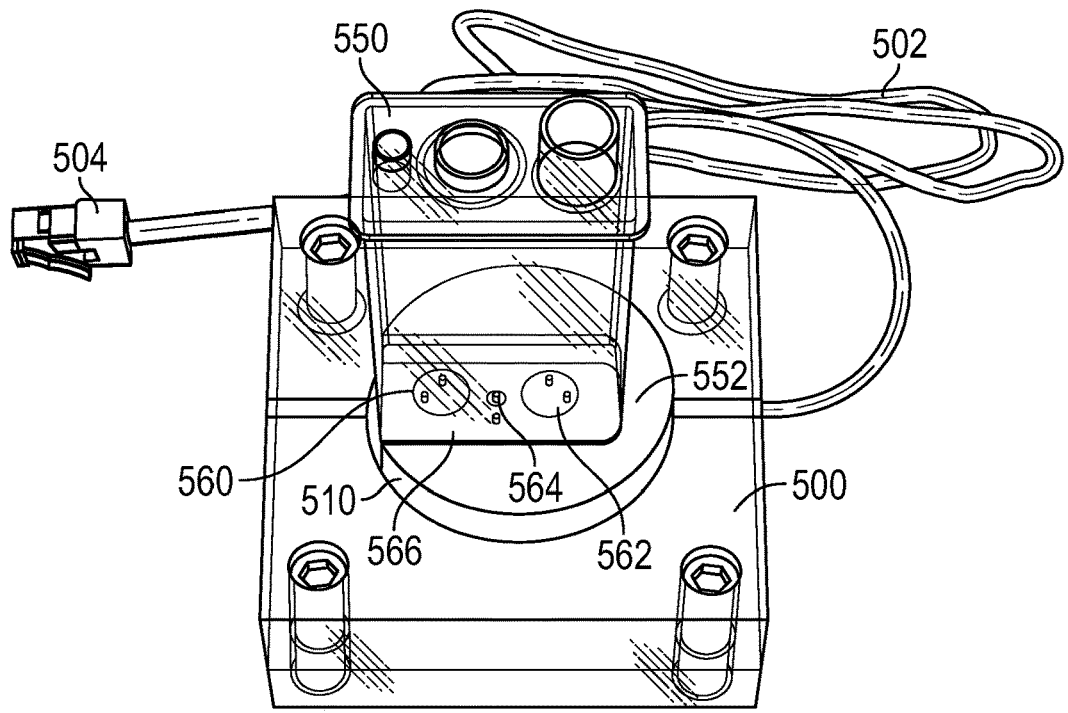

With continued reference to FIGS. 14A and 14B, in some embodiments a reaction vessel 550 is provided for compatible use with docking station 500. In some embodiments, reaction vessel 550 comprises a removable or non-removable lid that encloses an interior volume. The interior volume further includes a sensor interface 552 having a plurality of optimized solid-state electrodes that are exposed to the interior volume, such that a liquid or other material that is placed within the interior volume will contact the plurality of electrodes. In one embodiment, a reaction vessel 550 is provided having a sensor interface 552 comprising an AIM electrode 560, and ASM electrode 562, a RE 564, and a CE 566, wherein sensor interface 552 forms a bottom surface of the reaction vessel 550.

Figure 14C:
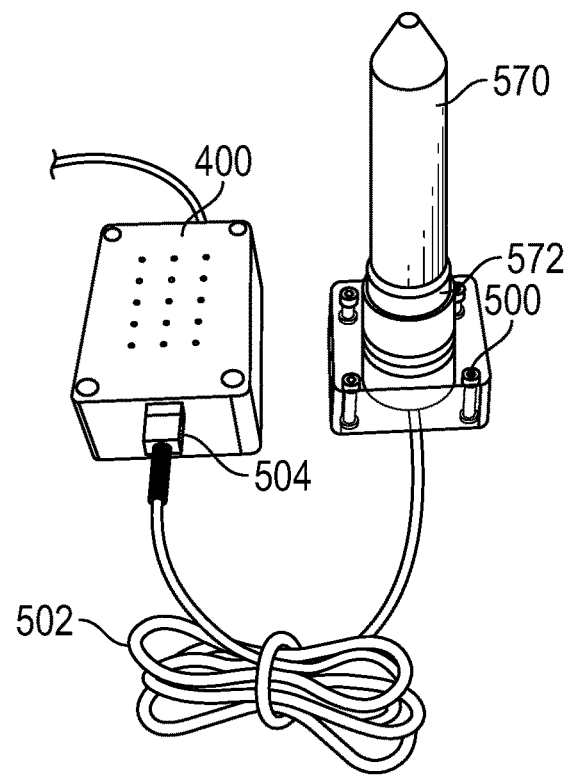

In one embodiment, a single use reaction vial 570 is provided having a lid 572 in which is incorporated a sensor interface having a plurality of solid-state electrodes, as shown in FIG. 14C. In one embodiment, reaction vial 570 is configured for use in a laboratory process. The plurality of solid-state electrodes is located on an interior surface of lid 572 and further comprise external contacts located on the outer surface of lid 572. When vial 570 is inverted and placed onto docking station 500, a liquid or other analyte material inside vial 570 contacts the inner surface of lid 572 thereby permitting contacts 520 of docking station 500 to receive electrical signals from the plurality of solid-state electrodes located on lid 572.

Figure 14D:
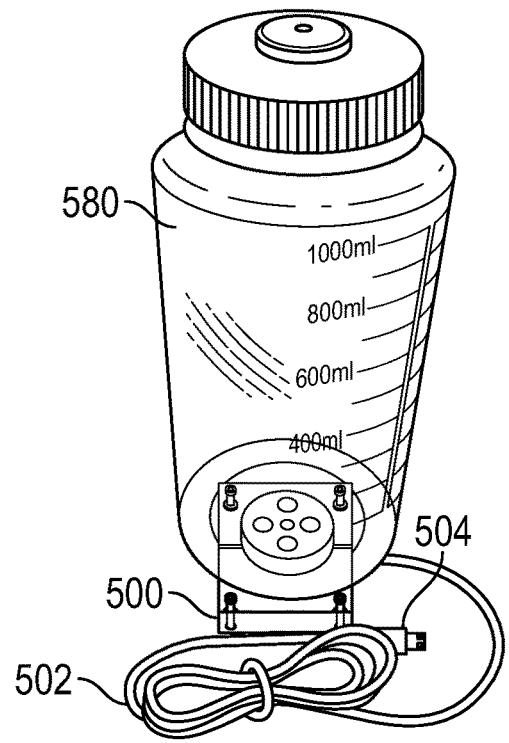
Figure 14E:
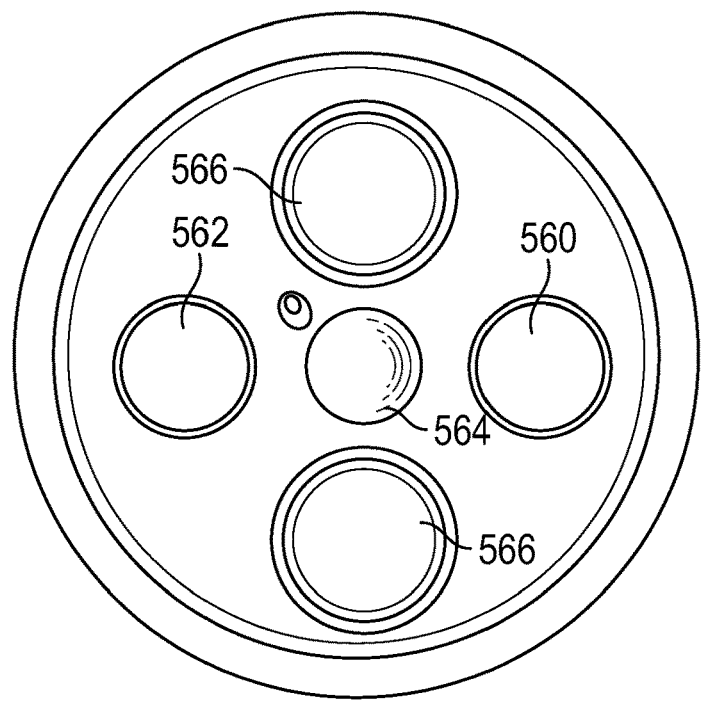
FIG. 14E is a detailed plan view of the sensor assembly of chamber 508 shown in FIG. 14D in accordance with a representative embodiment of the present invention.

In one embodiment, the present invention comprises a pre-pilot scale reaction chamber 580 having a solid-state sensor interface incorporated into the bottom surface of the chamber 580, as shown in FIG. 14D. The sensor interface comprises a plurality of solid-state electrodes that are operably coupled to respective contacts located on the outer surface of the chamber's bottom, such that when chamber 580 is placed on docking station 500, the external contacts are aligned with contacts 520 of docking station 500, thereby permitting communication between the plurality of optimized solid-state electrodes and docking station 500.

Integrated Sensor Interface

Various embodiments of the present invention comprise a sensor interface configured for incorporation into a container or packaging designed to retain an analyte-containing material or solution. Referring now to FIGS. 15A-15H, various sensor interfaces are shown having one or more features configured to assist in mounting or integrating the sensor interfaces into or onto a desired surface of a container.

Figure 15A:
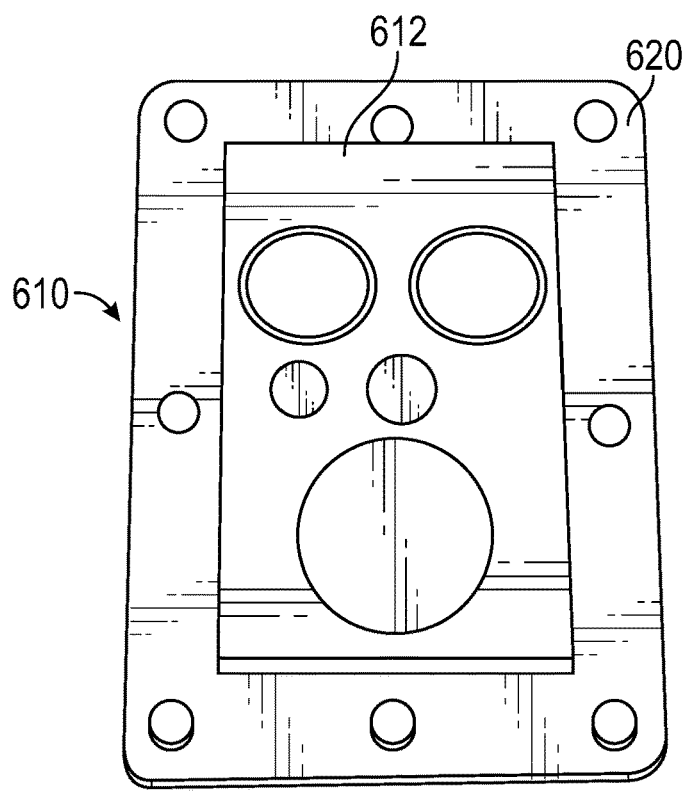
FIGS. 15A-15H show perspective views of various sensor interfaces for use in a variety of products and sample containers in accordance with representative embodiments of the present invention.
Figure 15B:
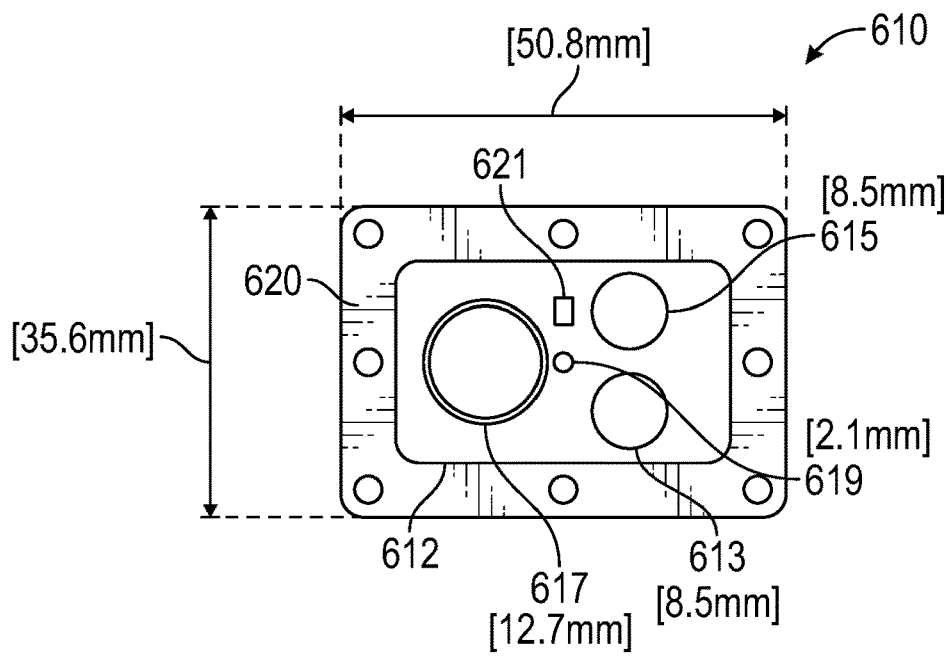
Figure 15C:
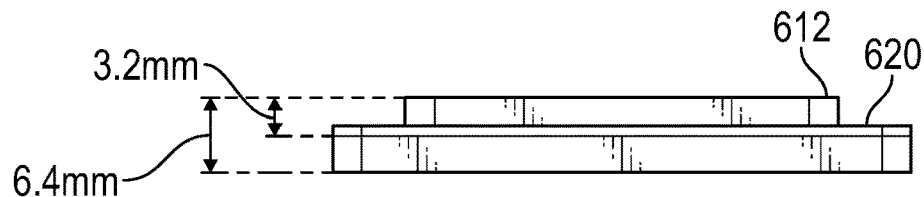
Figure 15D:
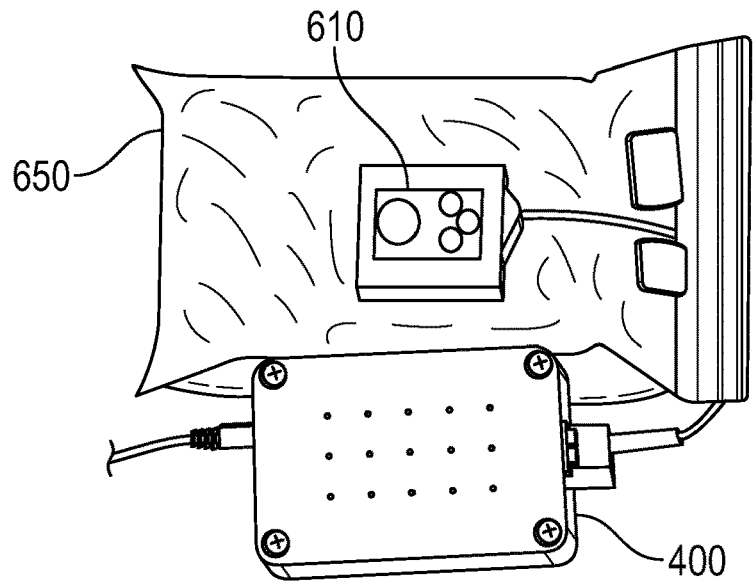
Figure 15E:
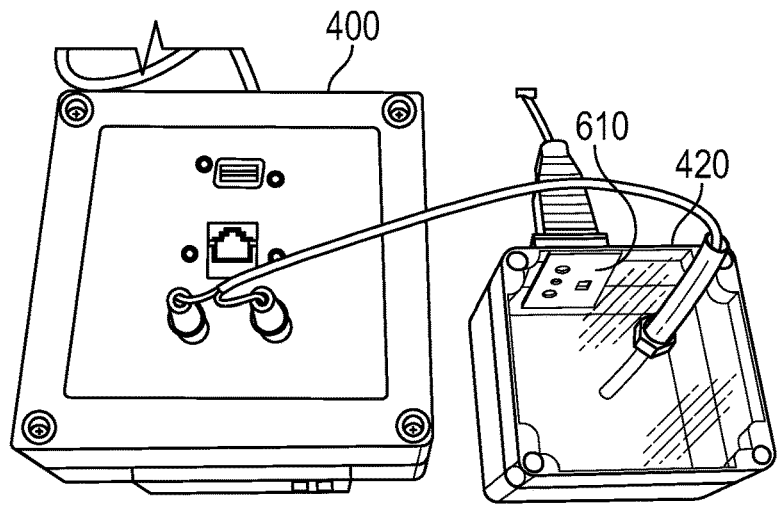

In some embodiments, sensor interface 610 comprises a flange 620 that extends outwardly from platform 612 to provide a mounting surface for a desired container. In some embodiments, flange 620 or another mounting surface is coupled to the desired container by at least one of mechanical interference, threading, welding, plastic welding, glue, adhesive, epoxy, mechanical clamp, a fastener, or any other known fastening method or device. Sensor interface 610 is generally integrated into a surface of a desired container such that sensor platform 612 is positioned within an interior of the container, so as to be in contact with the contents of the container. In some instances, sensor interface 610 is incorporated into a flexible wall surface of a single use bioreactor bag 650, as shown in FIG. 15D. Alternatively, sensor interface 610 may be incorporated into a rigid wall surface of a development and test system 420, as shown in FIG. 15E.

Figure 15F:
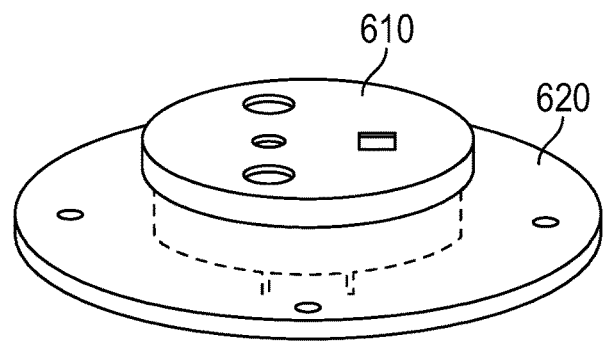
Figure 15G:
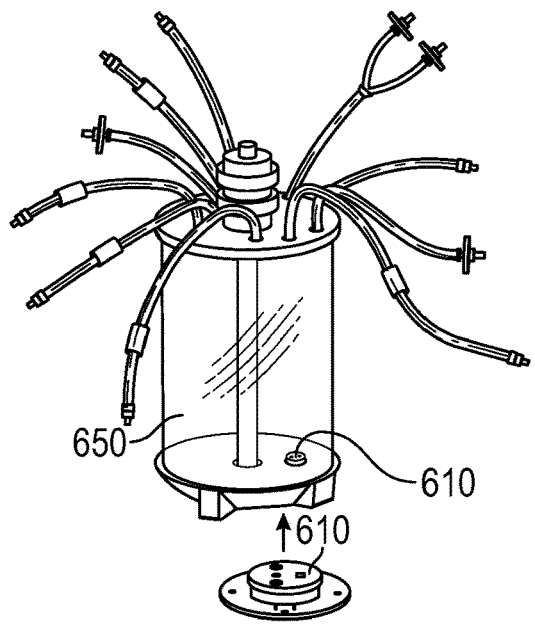
Figure 15H:
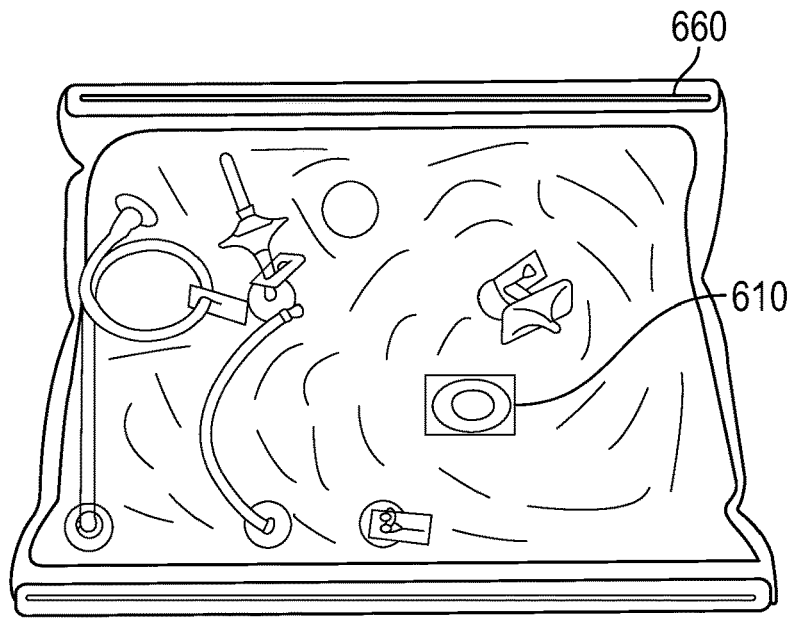

Sensor interface 610 may further comprise any shape and/or size configured to accommodate integration of the interface into a desired container or product platform. For example, in some embodiments sensor interface 610 comprises a round shape, as shown in FIGS. 15F-15H. In some instances, a round shape may be desirable for incorporating sensor interface 610 into containers having a round surface, such as the bottom surface of the bioreactor vessel 650 shown in FIG. 15G. Sensor interface 610 may also be rectangular, as may also be desirable for incorporation into a flexible side surface of a cellbag 660, as shown in FIG. 15H, or a rigid wall surface of a development and test system 20, as shown in FIG. 15E.

The various sensor interfaces 610 of the present invention further comprise a raised sensor platform 612 on which is arranged a plurality of solid-state electrodes. In some embodiments, one or more of these solid-state electrodes is optimized according to one or more methods of the present invention.

The arrangement, size, proximity, and materials of the solid-state electrodes of sensor interface 610 may be selected in order to provide an optimized sensor assembly, device or module in accordance with the present invention. For example, in one embodiment sensor platform 612 includes an IE comprising an AIM disc 613 having an exposed surface diameter of approximately 8.5 mm In one embodiment, AIM disc 613 comprises a carbon fiber epoxy material (Dragon Plate or ACP Composites). Sensor platform 612 further includes a WE comprising an ASM disc 615 having an exposed surface diameter of approximately 8.5 mm In one embodiment, ASM disc 615 comprises a carbon fiber epoxy material (Dragon Plate or ACP Composites). In one embodiment, Sensor platform 612 further comprises a CE 617 comprising a 316 grade stainless steel material and having an exposed surface diameter of approximately 12.7 mm In some instances, CE 617 is positioned on a side of platform 612 that is opposite AIM disc 613 and ASM disc 615, yet is aligned approximately between or in the middle of the two disks. In some embodiments, platform 612 further comprises a PRE 619 that is centrally located on platform 612 and at a position approximately centered between AIM disc 613, ASM disc 615, and CE 617. In one embodiment, PRE 619 comprises an exposed surface diameter of approximately 2.1 mm. Further, in one embodiment platform 612 comprises a thermistor 621, such as a surface mount thermistor.

Thin Film Sensor Assembly

Some embodiments of the present invention comprise a sensor assembly incorporated into a planar structure that is easily integrated into bottles, bags, balloons, flow cells, and other like surfaces. In one embodiment, the thin film sensor assembly comprises packaging material for storing a food item. In one embodiment, a sensor assembly comprises a low profile packaging material 700 having a profile thickness of approximately 2 mm or greater, as shown in FIG. 16.

Figure 18:
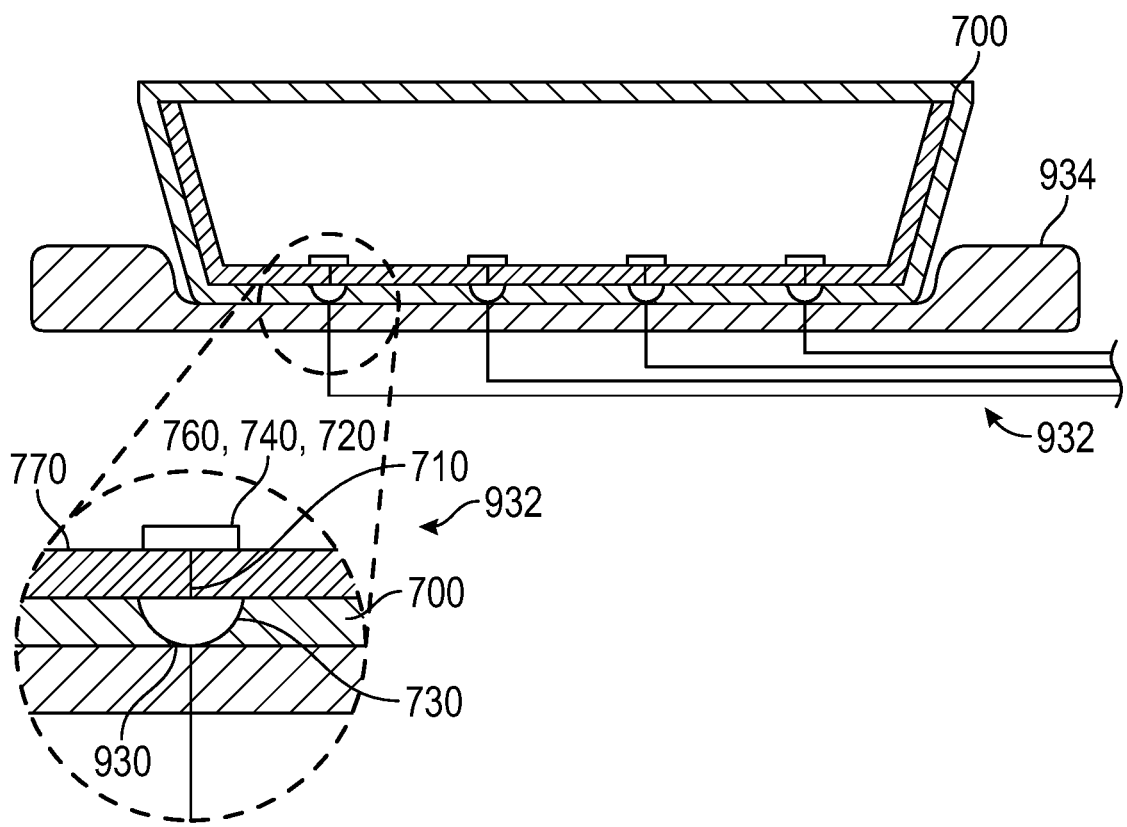
FIG. 18 is a cross-section side view of a product package having a plurality of sensors and a compatible reader device in accordance with a representative embodiment of the present invention.

In one embodiment, the sensor assembly is a microsensor assembly comprising small area electrodes that may be integrated into a variety of materials to measure very small volumes of analytes. For example, in one embodiment a microsensor assembly is provides which includes an AIM electrode 720, a CE 740, and an ASM electrode 760 incorporated into the thickness of packaging material 700, wherein the various electrodes are presented in proximity to a first or top surface 770 of the packaging material, and are coupled to electrical contacts 730 that are presented on a bottom or second surface 790 of the packaging material 700, wherein the second surface 790 is opposite the first surface 770. In some instances, electrical contacts 730 are operatively or electrically coupled to their respective electrode component via electrical circuits 710. In some instances, the top surface 770 further comprises a thermistor 750. Further still, in some instances packaging material 700 comprises a PRE 780 which spans the thickness of the material. Thus, electrical signals from the various electrodes may be detected by contacting the electrical contacts 730 with a compatible reader device. In some instances, a compatible reader device 932 comprises a surface 934 for receiving packaging material 700, wherein the surface 934 comprises a defined parameter to receive packaging material 700 in such a manner as to achieve proper alignment of electrical contacts 730 with correlating contacts 930 on the surface 934 of the reader device 932, as shown in FIG. 18.

Figure 16:
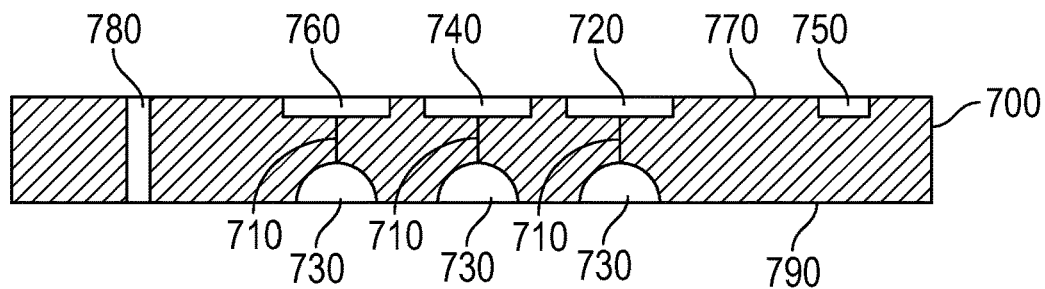
FIG. 16 is a cross-section side view of packaging material comprising a plurality of sensors in accordance with a representative embodiment of the present invention.

With continued reference to FIG. 16, in some instances the sensor assembly is provided by drilling or otherwise providing holes in packaging material 700, wherein the electrode material is plated into or otherwise filled into the holes. In some instances, such as for AIM and ASM electrodes 720 and 760, the electrodes comprise a graphite fiber composite that is machined and then fitted into the provided holes. In some embodiments, CE 740 comprises a piece of sheet metal that is fitted into a provided hole. Similarly, PRE 780 may comprise a sintered wire that is inserted into a provided hole. Thermistor 750 may comprise any compatible thermally sensitive resistor. In one embodiment, thermistor 750 comprises a 0402 surface-mount thermistor having dimensions of 0.4 mm×0.2 mm and a power rating of approximately 0.031 watts.

Figure 17:
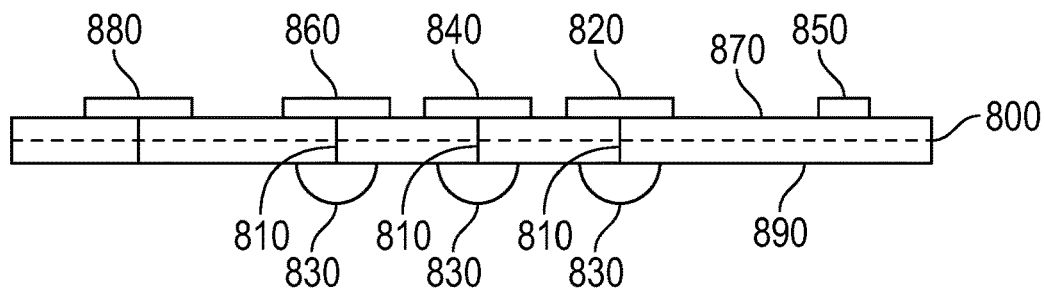
FIG. 17 is a cross-section side view of thin-film packaging material comprising a plurality of sensors in accordance with a representative embodiment of the present invention.
Figure 19:
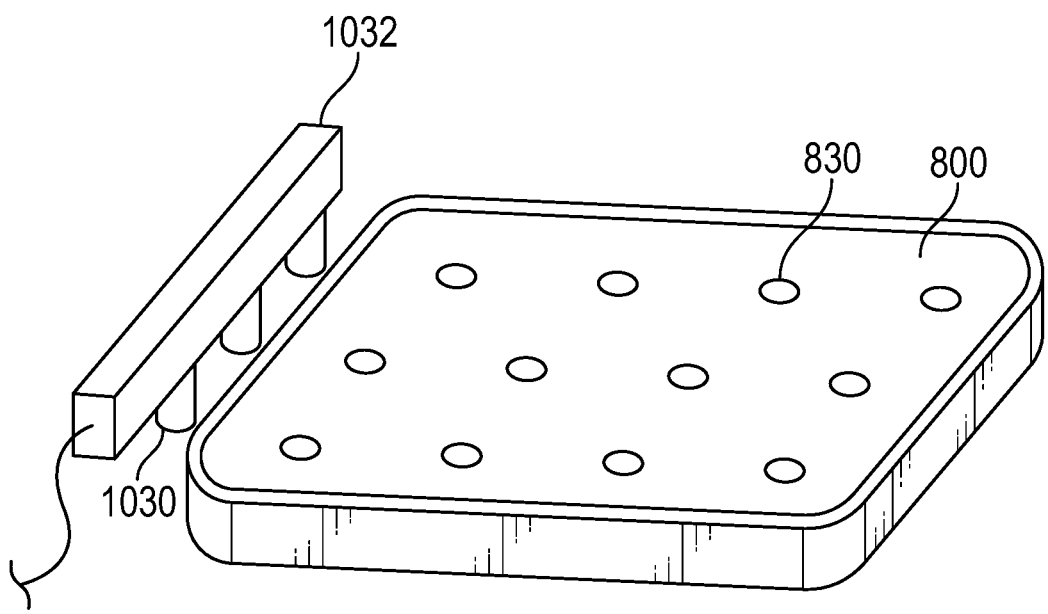
FIG. 19 is a perspective view of a product having a thin-film packaging and a scanner having integrated contacts in accordance with a representative embodiment of the present invention.

In another example, a sensor assembly of the instant invention is incorporated into a planar profile or thin-film packaging material 800 having a profile thickness of less than 2 mm, as shown in FIG. 17. Thin-film packaging 800 may comprise a flexible material, such as a plastic wrap or Kapton flexible substrate material. A thin-film packaging material 800 in accordance with the present invention may be scalable and adaptable to a roll-to-roll manufacturing process, with an interconnected network system which allows for monitoring of packaged items, such as food, on a docking station to indicate freshness based on pH. The thin-film packaging material 800 includes a sensor assembly comprising an AIM electrode 820, a CE 840, and an ASM electrode 860 is surface mounted onto a top surface 870, and electrically coupled to contacts surface mounted to a bottom surface 890 via electrical circuits 810. In some instances, top surface 870 further comprises a thermistor 850. Further still, in some instances thin-film packaging material 800 comprises a surface mounted PRE 880. Thus, electrical signals from the various electrodes may be detected by contacting the electrical contacts 830 with a compatible reader device 1032, as shown in FIG. 19. In some instances, reader device 1032 comprises a scanner having integrated contacts 1030 for sensing or reading electrical contacts 830 as part of a process for monitoring a product or material that is at least partially enclosed within packaging material 800, as shown in FIG. 19. In some instances a reader device is incorporated into a conveyor belt that is used to transfer a product or material that is at least partially enclosed within packaging material 800.

With continued reference to FIG. 17, in some instances the sensor assembly is provided by providing holes in thin-film packaging material 800, such as by laser ablation. The electrode material and other related components are then plated into or otherwise filled into the holes. In some instances, such as for AIM and ASM electrodes 820 and 860, the electrodes comprise graphite that is applied either through a screen printable paste or ink material. In some instances, CE 840 is sputter coated onto material 800, using a compatible material, such as Cr—Au or Ti—Pt. In some embodiments, PRE 880 is applied to material 800 as a screen printable silver compound. As with thermistor 750, thin-film material 800 may further comprise a thermistor 850 comprising a compatible thermally sensitive resistor, such as a 0402 surface-mount thermistor.

In some instances, a sensor assembly is incorporated into a low profile packaging material 700 for volume handling (such as a tray, discrete or snap singulation, as shown in FIG. 18) or an integration platform (such as a molded sheet). In some instances, a sensor assembly is incorporated into a thin-film packaging material 800 comprising a roll fabrication (such as a roll of plastic wrap, as shown in FIG. 19) or an integration platform (such as a Kapton flexible circuit). In some instances, the plurality of electrodes and corresponding circuitry is incorporated into one or more adhesive labels that are applied to an outer and/or inner surface of the thin-film material 800, wherein the electrodes and circuitry is accessible either across the thin-film material or through holes provided in the thin-film material.

In some instances, a sensor assembly comprises a monolithic structure, wherein each individual electrode is assembled into a single structure or housing. In other instances a sensor assembly comprises a multi-component sensor assembly that is operatively connected via one or more electrical circuits. In some instances, a sensor assembly comprises a multi-component sensor assembly, wherein at least some of the various components of the assembly are operatively connected via one or more wireless circuits. For example, in one embodiment a first sensor assembly comprising an IE is operably connected to a second sensor assembly comprising a WE via a wireless interface. In one embodiment, a first sensor assembly and a second sensor assembly are independently coupled to a compatible reader device via a wireless interface. Further, in one embodiment a first sensor assembly and second sensor assembly are operably interconnected via a wired or wireless interface, and further operably connected to a compatible reader device via a wireless interface.

Conductive substrates may be further supported using robust supporting materials such as ceramic, glass, or glass fiber-reinforced composites commonly used for printed circuit boards. These materials provide well-established connectivity options for transferring signals from the sensing elements to the electronic circuitry. Various packaging options (such as multilayer printed circuit boards, plate-through contacts etc.) offer increased packaging density, reliability, and functionality of sensors and devices.

Interactive Sensor Management System

Embodiments of the present invention further comprise an interactive sensor management system configured to receive, analyze, monitor and/or report signals generated from the various sensor assemblies, devices and modules of the present invention. The signals of the solid-state electrodes, sensor assemblies, devices and modules of the present invention are generated using Square wave voltammetry methods, as disclosed in WO/2010/104962, WO/2010/111531, WO/2010/118156, WO/2013/112767, WO/2013/134582, WO/2014/106066, and WO/2015/191924, each of which is incorporated herein by reference. In some instances, these generated signals are received by the interactive sensor management system for further analysis and processing, as may be desired for a specific application.

In some instances, the management system maximizes the accuracy and longevity of the optimized electrodes by implementing application specific test profiles and internal standards based on an intended use for the optimized electrodes. For example, in one embodiment a test profile or other parameter of the management system is adjusted to achieve a desired signal level from an optimized electrode having a known or unknown current density. In one embodiment, a test profile or other parameter of the management system is adjusted to achieve a uniform signal level from a plurality of electrodes, wherein each electrode comprises a unique current density. Thus, the management system is capable of tuning an output signal for an optimized electrode, regardless of the current density of the electrode.

In some instances, the management system adaptively learns a test environment to accurately predict and/or recommend optimal test profiles and internal standards for one or more product platform devices. In some instances, the management system uses at least one optimization technique (e.g., statistical) to improve the accuracy of collecting and analyzing data from one or more optimized electrodes. In some instances, the management system provides a user-friendly, intuitive display and one or more test status monitoring features, such as, for example, a warning alarm or a generated email. In some instances, the management system comprises one or more quality control features for detecting and reporting system or testing errors, such as, for example, sensor incompatibility, product development kit variations, or exceeding a threshold level or value. In some instances, the management system is configured to monitor and manage system level traceability. In some instances, the management system comprises features for executing scheduled test runs. In some instance, the management system is capable of remote operation.

Square wave voltammetry (SWV) methods are used to generate signals from sensor components of the present invention. Signals generated by the WE and the IE can be monitored simultaneously or at different intervals. In the current context, the terms "sweep" and "scan" are used interchangeably. In embodiments where both the ASM and the AIM are located on the same substrate, a square-wave potential sweep is applied to elicit separate but contemporaneous responses from the ASM and the AIM. The same scan parameters (such as the range of voltage sweep, pedestal height, and interval between scans, also referred to as dwell time) are applied to both electrodes.

In other embodiments where the ASM and the AIM are located separately on discrete, electrically independent electrodes, two separate square-wave potential sweeps with different scan parameters can be applied to the electrodes. Sampling the WE and IE separately offers several benefits. First, signal quality can be individually optimized for the ASM and for the AIM. Second, the IE can be sampled less frequently than the WE some AIMs are designed to remain unchanged in different analytes. Thus, the IE only needs to be sampled to reconfirm stasis when a change in analyte takes place or is expected. Time that is not spent on sampling the IE can be used to resume monitoring of the WE, in effect shortening the WE dwell time and resulting in a more responsive pH measurement system. Third, less frequent sampling of the IE allows certain AIM materials to be employed that exhibit good accuracy and broad pH-insensitivity ranges but are susceptible to signal loss as a result of repetitive electrochemical excitation.

Figure 20:
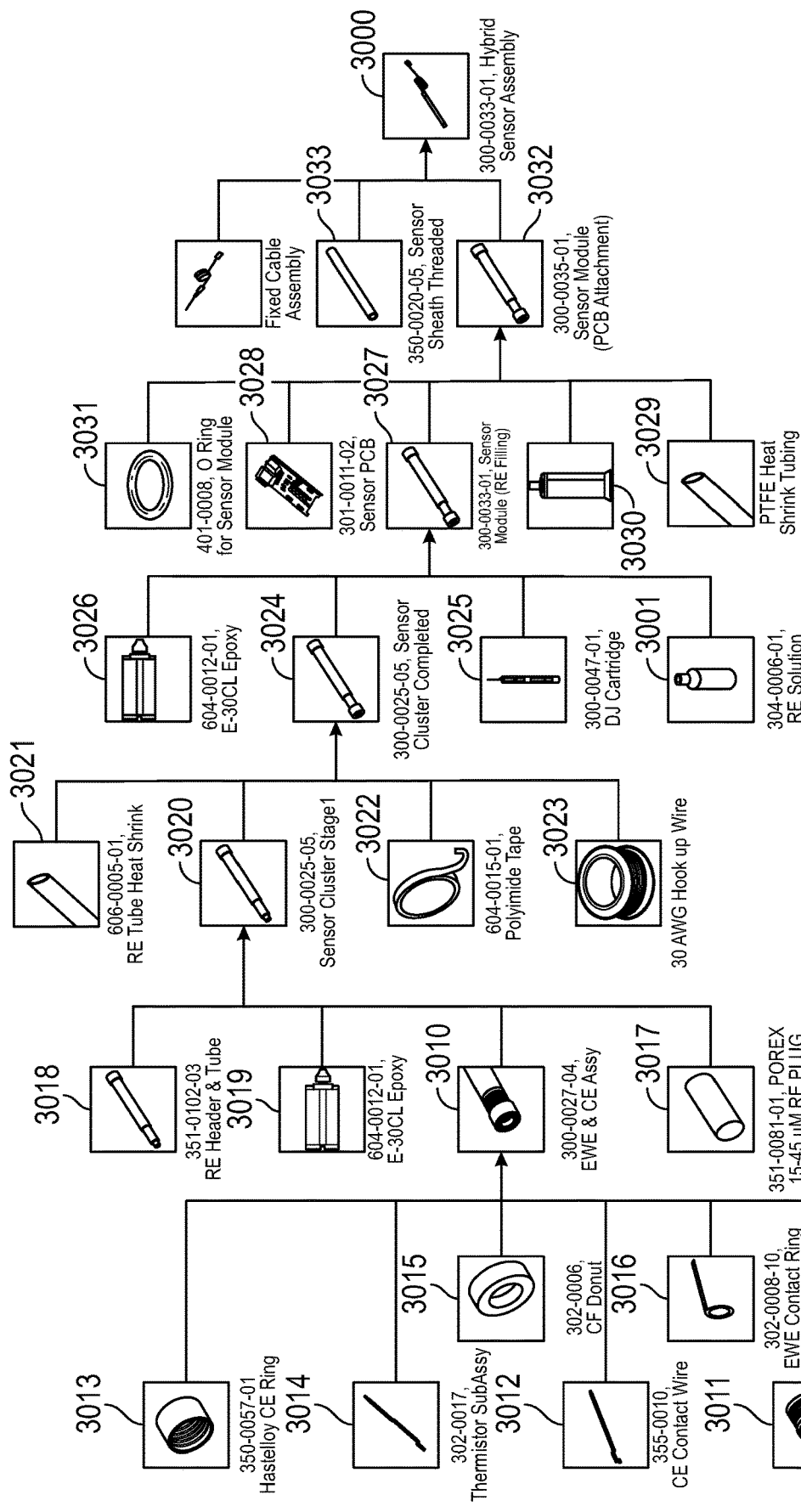
FIG. 20 is a diagram illustrating the operation of SWV electronics of sensors in accordance with representative embodiments of the present invention.

In some embodiments, SWV electronics of sensors of the invention are configured to multiplex between the inputs from the WE and the IE. The WE and IE inputs are electrically equivalent and are in common with the reference electrode/pseudo reference electrode (RE/PRE) and CE circuits. The operation of this system is illustrated in FIG. 20.

The differentiating feature of the potentiostat circuitry (Blocks 1 to 9) is a multiplexer (3), used to select either the ASM or AIM electrodes. The transimpedance amplifier (4), analog-digital converter (ADC) (5), Reference Electrode (6), digital-analog converter (DAC) for generating the square wave excitation (7), and Difference Amplifier (8) that drives the Counter Electrode (9) are common to both the WE the IE.

The SWV operating parameters, including voltage scan (or sweep) range, pedestal height, equilibration time, and dwell time (i.e. rest time between sequential voltage scans), are independently adjustable for the WE and IE. In one embodiment, the same SWV circuit is used to monitor the WE and IE sequentially.

Figure 21:
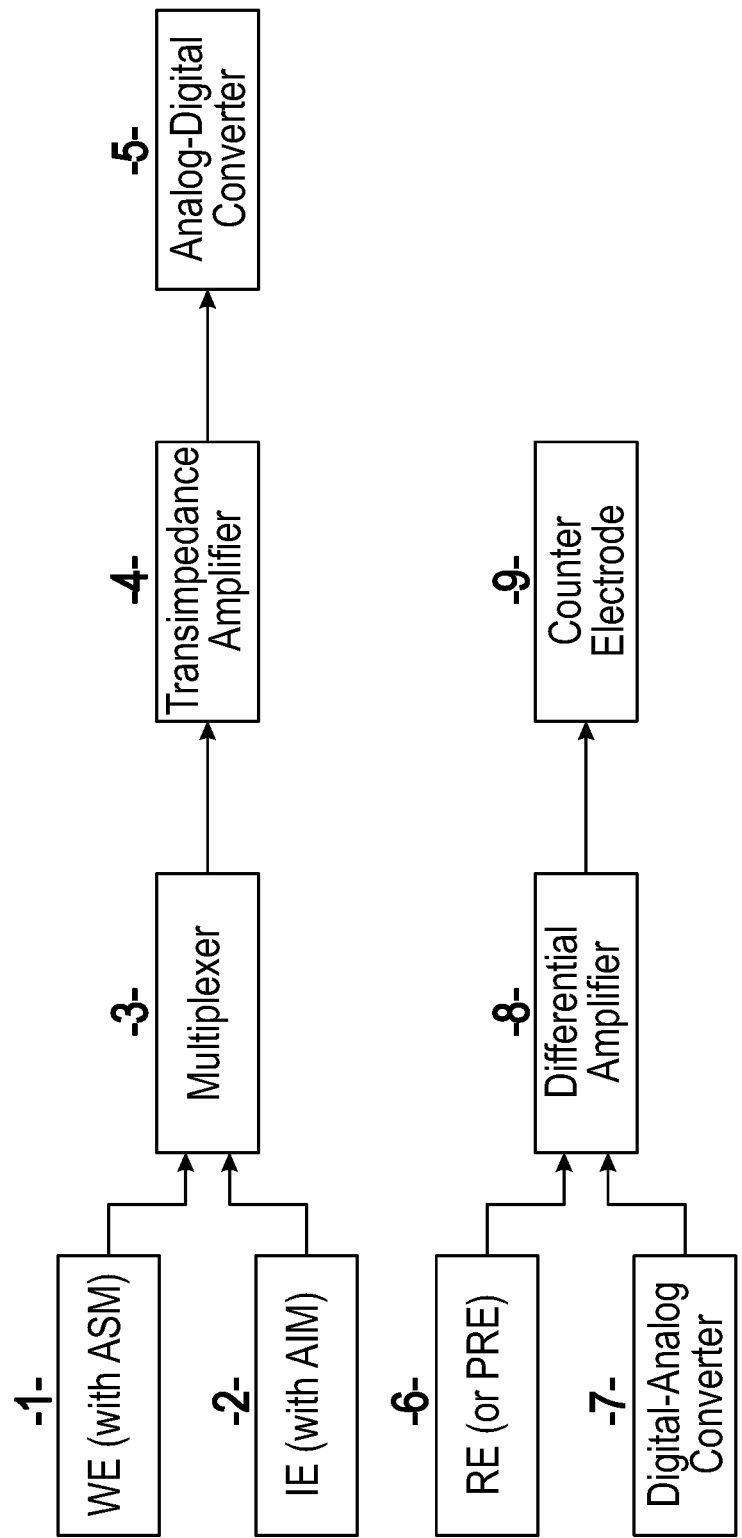
FIG. 21 is a diagram illustrating overall time sequence of WE and IE scan in accordance with representative embodiments of the present invention.

The overall time sequence of WE and IE scan is shown in FIG. 21. Arrows represent grouping of scans, or repetitions, occurring at regular intervals set at independent dwell times.

The scan parameters are optimized for each electrode. Statistics, i.e. peak potential averages and standard deviations of a series of repetitions of scans, can be kept separately for the WE and IE so that the results from these electrodes can be independently analyzed.

Operating parameters for the SWV for the WE and IE of the present invention, including typical ranges and preferred values, are shown in Table 3.

A special feature of the SWV technique of the invention is the implementation of two operating modes. First, a "seek" mode is used at the beginning of each voltage scan covering a relatively broad potential range in order to locate the peak potential of the ASM or AIM in the analyte. Second, a "tracking" mode is used with smaller voltage increments in order to locate the peak potential from the electrode at higher resolution. In the tracking mode, for example, the step height of 2 mV corresponds to a pH resolution of 0.03 pH units. This is sufficient for most pH analysis applications. It is possible to reduce the step height further to 1 mV (for a resolution of 0.015 pH unit), but doing so also increases the time needed to span the ±200 mV range. A narrower scan width is sufficient for the AIM peak potential is largely invariant.

The following procedure describes how the signals from the WE and the IE are used to derive the concentration of the analyte of interest, in this case the hydronium ion concentration expressed as pH.

Figure 22:
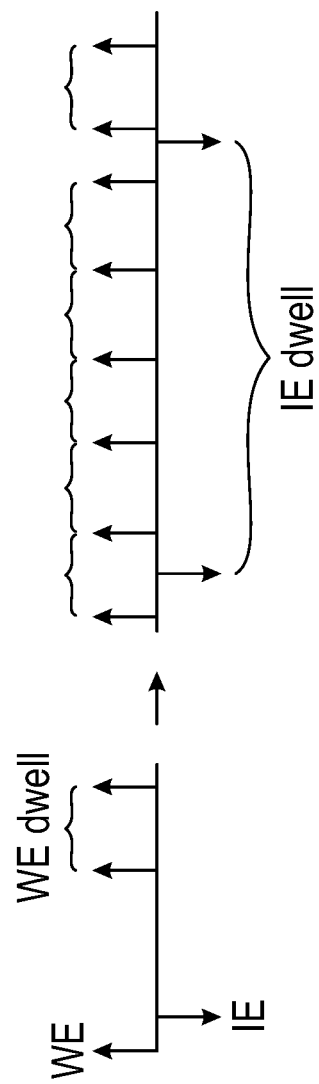
FIG. 22 is a diagram illustrating WE scan, baseline correct, peak pick, calculate ASM peak potential, and ASM correction in accordance with representative embodiments of the present invention.
Figure 23:
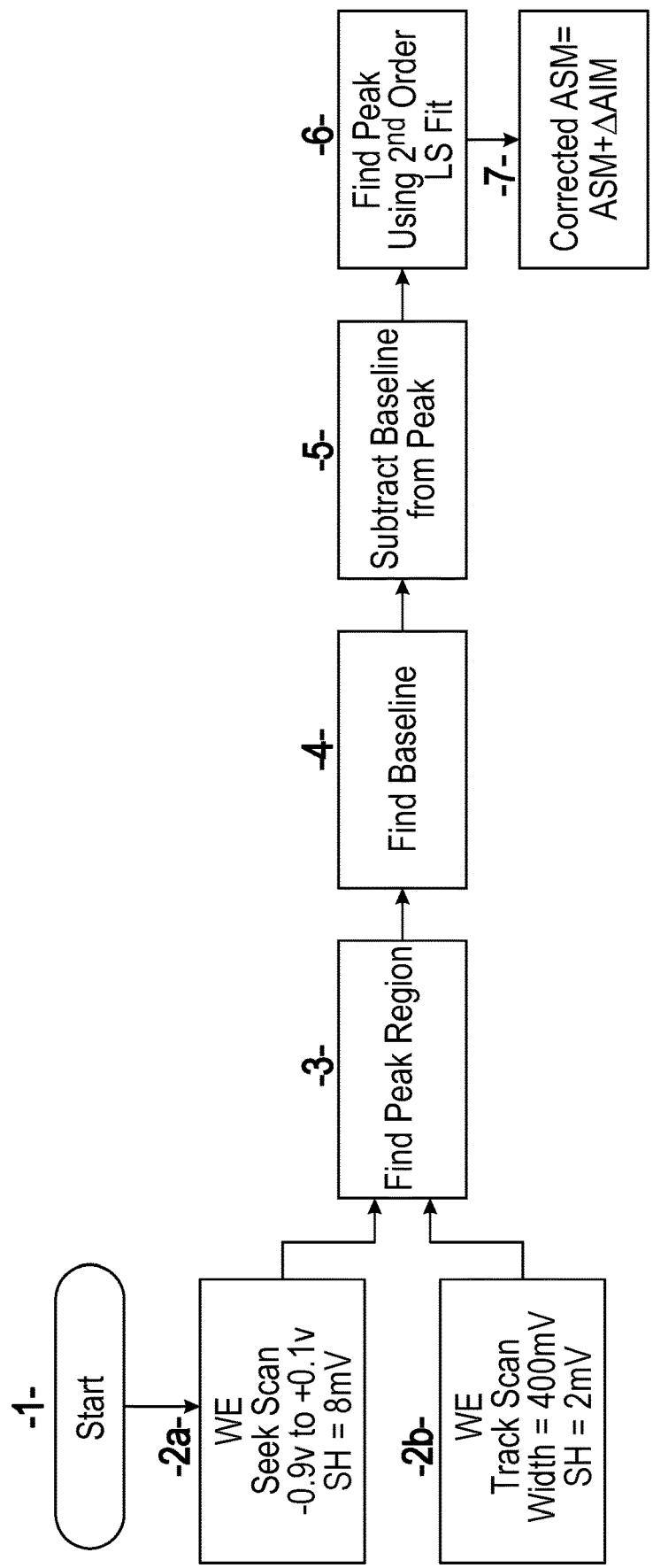
FIG. 23 is a diagram illustrating IE scan (baseline corrected, peak-picked) used to calculate AIM peak potential and ΔAIM in accordance with representative embodiments of the present invention.

As shown in FIGS. 22, 23 and Table 4, the start of the scan (1) begins with a wide SWV sweep of the WE at low resolution (2a) to seek the center of subsequent WE tracking scans (2b). The rate of the sweep is set by the step height (SH) of each voltage increment between the limits of the voltage range. Processing the SWV output to find the peak is summarized in steps 3 through 6. Just after the WE seek scan (2a), but before commencement of the WE tracking scans (2b), a wide SWV sweep of the IE (8a) seeks the center of subsequent IE tracking scans. The initial group of IE tracking scans are averaged to determine the AIM Baseline (9) and saved into non-volatile memory (10). The difference of the peaks (steps 3-6) of subsequent AIM tracking scans (8b) from the AIM Baseline is equal to ΔAIM (11). Because the AIM peak is invariant, ΔAIM reflects the drift of the RE or PRE. The ASM peak is corrected by ΔAIM (7), applied as a correction factor equivalent to the drift of the RE or PRE. The calibration table characterizes the average ASM response to standard buffers over a pH ranging (e.g. from pH 2 to pH 12) at several temperatures (e.g. from 5° C. to 50° C.). Entries for calibration table are made under controlled conditions, using a stable RE, such as Ag/AgCl or Calomel. From the calibration table, at the sensor temperature and the voltage equal to the Corrected ASM (7), the corresponding pH of the sample is determined (12).

TABLE 4

Calculate pH from predetermined calibration table (or function)

pH = f( Corrected ASM, Temperature)
-12-

TABLE 3

Operating parameters for SWV for WE and IE

| Parameter | Mode | WE (with ASM) | | IE (with AIM) | |
|---|---|---|---|---|---|
| | | Range | Preferred | Range | Preferred |
| Scan Rate | | 30 to 120 mV/s | 60 mV/s | 30 to 120 mV/s | 60 mV/s |
| Pedestal Height | | 1 to 150 mV | 100 mV | 1 to 150 mV | 25 mV |
| Step Height | Seek | 1 to 10 mV | 8 mV | 1 to 10 mV | 2 mV |
| | Tracking | | 2 mV | | 2 mV |
| Scan Width | Seek | −1000 mV to +100 mV | | −100 mV to +800 mV | −100 mV to +500 mV |
| | Tracking | Peak +/− 250 mV | | Peak +/− 200 mV | |
| Dwell | | 0 to 3600 s | 30 s | 0 to 3600 s | 1200 s |

Determining pH (or other analyte concentration) with a WE-IE pair of the invention can be performed as follows. A calibration table of the response of the ASM to pH buffers over the temperature range referenced to a standard Ag/AgCl or calomel reference electrode can be used, enabling correcting the ASM peak in response to the drift of the AIM. Another method is to prepare the calibration table directly from the difference between the ASM and AIM peak potentials to pH buffers over a given temperature range. These operations can be incorporated in the firmware of an analyte sensing device of the invention.

An analyte sensing device of the invention comprises a sensor assembly comprising at least one each of WE, IE, RE (CRE or PRE, but typically a PRE), and CE. These sensor components can be configured in various spatial arrangements, surface area ratios, planar or three-dimensional designs, in coaxial or non-coaxial geometries, or some combination thereof, as discussed previously.

Various aspects of the invention are also illustrated in the following examples.

EXAMPLES

Example 1: Synthesis of PVA-AQ

A suitable solid-state electrode for use in one or more sensor assemblies, devices, modules, or product platforms of the invention was prepared from a hydrogel composed of poly(vinyl alcohol) covalently bonded to an anthraquinone derivative (PVA-AQ). PVA-AQ was synthesized using diethyl amino methyl polystyrene: a polymeric base commonly used in organic synthesis reactions. This reaction generally requires approximately 48 hours to complete. To shorten the reaction time, the present invention provides a method in which n-butyl lithium, sodium hydride and potassium tertiary butoxide are reacted, however, any of a number of bases commonly used in organic synthetic reactions may be substituted and reaction conditions modified as needed to make a desired PVA-AQ, including any substitution to change the reaction time and/or density of AQ functionalization, in accordance with the present invention. Accordingly, the methods and PVA-AQ chemistries of the present invention may be tailored by using several different bases to achieve the functionalization of PVA desired for a particular application. An exemplary synthesis of PVA-AQ using n-butyl lithium as a base is shown in Table 5.

TABLE 5

PVA-AQ Synthesis using n-butyl lithium

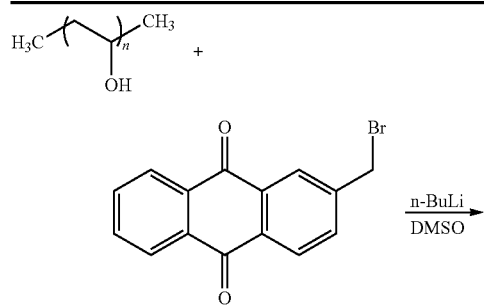

TABLE 5-continued

PVA-AQ Synthesis using n-butyl lithium

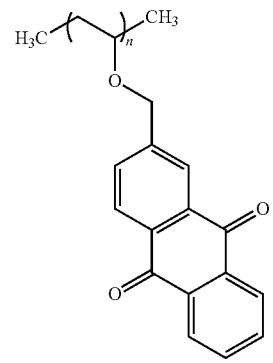

A. Synthesis of PVA-AQ using n-butyl lithium as a base

The procedure for preparing the PVA-AQ of Table 5 is as follows. An oven dried 500 ml flask with a stir bar was purged with argon for 30 min. 1.77 g (0.042 mol) PVA was added to flask along with 300 mL dry DMSO added via cannula transfer. The system was maintained under positive argon pressure and heated to 50° C. in an oil bath while stirring with magnetic stir bar to dissolve PVA. After two hours, the flask was cooled to room temperature and 10.4 mL (0.0166 mol) n-butyl lithium was added. After 15 minutes, 5 g 2-bromomethyl anthraquinone was added. This was left to stir for 20 hours under argon at ambient temperature. The following day, the murky brown, crude reaction mixture was dropped into 10x volume stirring of 1,4-dioxane. The resulting solution was caramel-brown with pale yellow solids. This solution was left to stir for two hours and then vacuum filtered on glass fritted Buchner funnel. Alternately, the mixture above may be allowed to settle and the pale yellow solids may be separated after removing the solvent mixture by decantation. Once removed, the solids were washed with acetone. The solids were again dissolved in DMSO, precipitated with 1, 4-dioxane and acetone to remove any unreacted bromomethyl anthraquinone. A hexane wash also used to help remove impurities.

B. Synthesis of PVA-AQ using sodium hydride as the base

An oven dried round bottom flask (flask 1) with a stir bar was left under argon for 30 min. 924 mg (21 mmol) of PVA was added to flask along with 50 ml of dry DMF added via cannula transfer. An oil bath was heated to 120° C., and the flask was placed in the oil bath to dissolve the PVA. Once the PVA is dissolved, the flask was removed from the oil bath and allowed to cool to room temperature. 20 ml dry DMF was added to a second oven dried flask (flask 2) via cannula transfer. Sodium hydride (400 mg, 10 mmols) was added to flask 2 and stirred. The contents of flask 2 were added to flask 1 via cannula transfer. The sodium hydride/PVA mixture of flask 1 appeared as a pale yellow suspension. After stirring for 20 min, bromomethylanthraquinone (300 mg, 1 mmol) was added to the reaction. After 5 minutes, the mixture turned deep yellow-brown with very little undissolved solids. This mixture was stirred for 90 min. 0.5 ml of water was added to quench the reaction and then stirred for an additional 30 minutes. 10.5 mL (10.5 mmols) of 1 M hydrochloric acid was then added to flask 1 which neutralized the deprotonated PVA to assist in solubilizing the mixture, the result of which caused the mixture to turn pale yellow. The contents of flask 1 were dropped into a new flask (flask 3) containing 1.5 L of acetone, and stirred for 15 minutes, during which a pale yellow precipitate formed. The precipitate was allowed to settle for 10 min and then decanted to reduce the precipitate's volume. The decanted precipitate was then vacuum-filtered on an ice bath. The solids were then washed with acetone and dried on vacuum.

Example 2: PVA-Fc Synthesis Using HCl

A suitable solid-state electrode for use in one or more sensor assemblies, devices, modules, or product platforms of the invention was prepared from a hydrogel composed of poly(vinyl alcohol) covalently bonded to a ferrocene derivative ("PVA-Fc"). PVA-Fc was synthesized by dissolving 2.0 g of poly(vinyl alcohol) ($4.55 \times 10^{-2}$ equivalents) in 50 mL of 1-methyl-2-pyrrolidinone ("NMP") by stirring, at room temperature, overnight. 500 mg of ferrocene carboxaldehyde ($2.34 \times 10^{-3}$ moles) was then added to the stirred solution. 1.0 mL of hydrochloric acid was then added, and the resulting solution was stirred at room temperature for 48 hours ("stirred solution"), after which an aliquot of this stirred solution was diluted in methylene chloride and examined by TLC (silica, 24% methanol in chloroform) which showed that the ferrocene carboxaldehyde was not completely associated with the PVA.

The polymer was precipitated by slow addition of the stirred solution into 250 mL of ethyl acetate under vigorous stirring. After the addition was complete, the ethyl acetate was removed by decantation. The remaining polymer was subsequently washed twice in 250 mL of ethyl acetate by stirring, to remove any remaining NMP and unbound ferrocene carboxaldehyde. The polymer was isolated by filtration, washed with ethyl acetate, and dried under vacuum, yielding 2.0 g. An exemplary synthesis of PVA-Fc using hydrochloric acid is shown in Table 6.

TABLE 6

PVA-Fc Synthesis using HCl

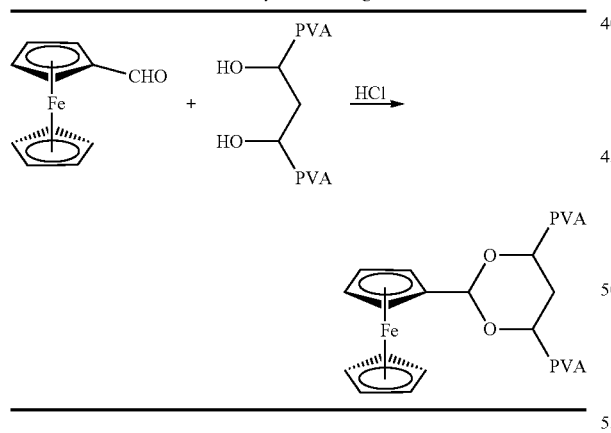

Example 3: PVA-Fc Electrode

A suitable solid-state electrode for use in one or more sensor assemblies, devices, modules, or product platforms of the invention is prepared from a hydrogel composed of poly-(vinyl alcohol) covalently bonded to a ferrocene derivative ("PVA-Fc"). The PVA-Fc hydrogel is formed and crosslinked directly on an electrode substrate by one or more methods of the present invention. In one instance, a carbon electrode substrate is first soaked in a wetting agent, such as Solutol® or polyethylene glycol, and subsequently transferred to a solution of poly(vinyl alcohol) for 4-10 hours. The soaked carbon substrate is then transferred to a solution of ferrocene carboxaldehyde in hydrochloric acid at 40-50° C., and stirred to coat the substrate. The coated carbon substrate is then heated at 120-150° C. to complete the synthesis and crosslinking of PVA-FC.

Example 4: PVA-Fc-MA Solid-State Electrode

A suitable solid-state electrode for use in one or more sensor assemblies, devices, modules, or product platforms of the invention is prepared from a hydrogel composed of poly-(vinyl alcohol) covalently bonded to a ferrocene derivative ("PVA-Fc"). The PVA-Fc hydrogel is formed and crosslinked directly on an electrode substrate by one or more methods of the present invention. In one instance, a carbon electrode substrate is first soaked in a wetting agent, such as Solutol® or polyethylene glycol, and subsequently transferred to a solution of poly(vinyl alcohol) for 4-10 hours. A PVA-Fc solution is prepared by dissolving ferrocene carboxyaldehyde in hydrochloric acid. Depending upon the degree of crosslinking and hydrophilicity desired, 5-20 wt % maleic anhydride is added to the PVA-Fc solution to provide a PVA-Fc maleic anhydride ("PVA-Fc-MA") solution. The soaked carbon substrate is then transferred to the PVA-Fc-MA solution and stirred at 40-50° C. to coat the substrate. The coated carbon substrate is then heated at 120° C. for one hour to complete the synthesis and crosslinking of PVA-FC-MA hydrogel on the carbon electrode substrate. An exemplary synthesis of PVA-Fc-MA is shown in Table 7.

TABLE 7

PVA-Fc-MA Synthesis

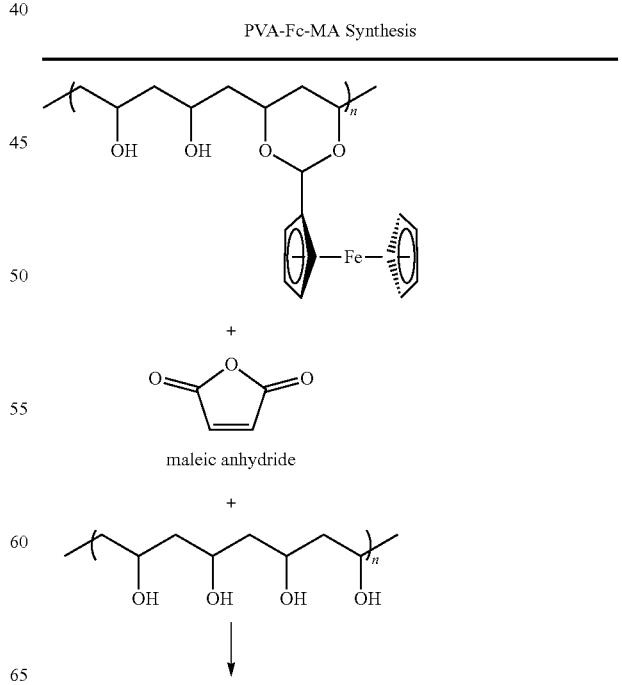

maleic anhydride

TABLE 7-continued

PVA-Fc-MA Synthesis

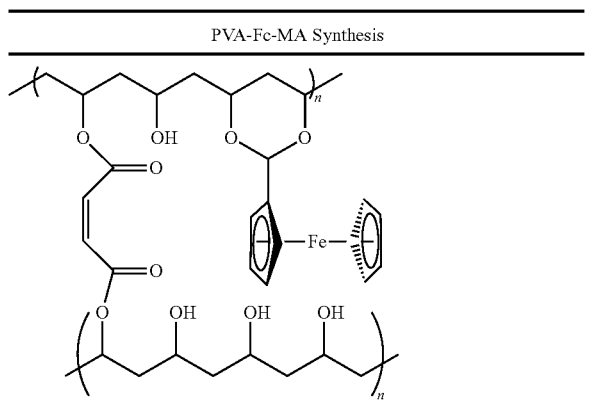

Example 5: Hybrid Sensor Assembly

A hybrid sensor assembly is provided comprising a hand-held probe assembly configuration, wherein a distal end of the probe assembly includes a sensor assembly comprising a plurality of optimized solid-state electrodes, in accordance with the present invention. In one embodiment, the hybrid sensor assembly is configured for laboratory use, as well as food and beverage applications. The RE of the sensor assembly comprises a Ag/AgCl gel coated polyethylene filter having a double junction and comprises a surface area of approximately 7.1 mm². The CE of the sensor assembly comprises a surface area of approximately 282.58 mm², which is approximately 8-times greater than the RASA of the ASM. The sensor assembly further comprises a WE comprising a 3-dimensional, donut-shaped substrate on which is coated an analyte sensitive material (ASM). The WE is recessed into the tip of the probe assembly such that the sides and back surfaces of the substrate are covered, thereby exposing only the frontal plane or face of the electrode. Depending upon the porosity of the substrate, the ASM-containing polymer may penetrate into the pores of substrate from the frontal plane, thereby creating a 3-dimensional web-like network therein. In one embodiment, the effective RASA of the one or more ASMs is determined to be approximately 37.55 mm² with an average current of 100 uA, and an average current density of 102 A/m².

In one embodiment, the ASM of the hybrid sensor assembly was tested at a scan rate of 60 mV/s with an amplitude of 100 mV at a frequency of 60 Hz. The average signal intensity/current generated by the ASM of the probe assembly was 220 uA, with an average current density of approximately 5.86 A/m².

In one embodiment, the hybrid sensor assembly comprises a minimum useful life of 21 days, and may exceed 1000 hours of use when stored at 25° C. in 3M KCl.

Example 6: Paddle-Like Sensor Tip

A sensor tip is provided having a paddle-like structure comprising two opposing planar surfaces and a single distal planar surface. In one embodiment, the sensor tip is configured for single-use. The single distal planar surface comprises a sintered Ag/AgCl RE having a surface area of approximately 12.26 mm². The CE of the sensor tip is made of Hastealloy and comprises a surface area of approximately 282.58 mm², which is approximately 8-times greater than the RASA of the ASM-containing WE. One opposing planar surface comprises a donut-shaped ASM-containing WE constructed of carbon fiber epoxy or vinyl ester/graphite epoxy coated with a polymeric ASM/PVA-AQ matrix material, and further comprising a RASA of approximately 37.42 mm². The other opposing planar surface comprises a flat, disc-shaped AIM comprising a RASA of approximately 57.42 mm².

The ASM of sensor tip was tested at a scan rate of 60 mV/s at a frequency of 60 Hz. The AIM of the sensor tip was tested at a scan rate of 30 mV/s with an amplitude of 25 mV at a frequency of 60 Hz. The average signal intensity/current generated by the ASM of the probe assembly was 220 uA, with an average current density of approximately 5.86 A/m². The average signal intensity/current generated by the ASM of the sensor tip is 220 uA, with an average current density of approximately 5.86 A/m². The average signal intensity/current generated by the AIM of the sensor tip is 400 uA, with an average current density of approximately 6.97 A/m².

In one embodiment, the disposable sensor tip comprises a minimum useful life of 25 days, and may exceed 50 days, or 1200 hours of use when stored dry at 25° C.

Example 7: Modified Sensor Tip

A modified sensor tip is provided for use in measuring analyte-containing solutions. In one embodiment, the sensor tip is configured for single-use. The sensor tip comprises a RE having a surface area of approximately 12.26 mm². The CE of the sensor tip comprises a surface area of approximately 282.58 mm². The sensor tip further comprises an ASM-containing WE comprising an arched, half donut-shaped substrate having a RASA of approximately 16.97 mm², with an average current of 150 uA, and a current density of 8.8 A/m². The sensor tip further comprises an AIM-containing IE also comprising an arched, half donut-shaped substrate having a RASA of approximately 16.97 mm², with an average current of 20 to 43 uA.

The ASM of the modified sensor tip was tested at a scan rate of 60 mV/s with an amplitude of 100 mV at a frequency of 60 Hz. The AIM of the sensor tip was tested at a scan rate of 30 mV/s with an amplitude of 25 mV at a frequency of 60 Hz. The average signal intensity/current generated by the ASM is 110 uA, with an average current density of approximately 6.48 A/m². The average signal intensity/current generated by the AIM is 40 uA, with an average current density of approximately 2.35 A/m².

In one embodiment, the sensor tip comprises a minimum useful life of 21 days without amplification, and may exceed 72 days of use when stored dry at 25° C.

Example 8: Planar Sensing Material

A planar sensing material is provided having rigid or flexible properties and comprising a plurality of solid-state electrodes in accordance with the present invention. In one embodiment, the sensor material is configured for single-use. The sensing material comprises an integrated RE comprising a surface area of approximately 12.26 mm². The CE of the sensing material comprises a surface area of approximately 126.45 mm². The sensing material further comprises an ASM-containing WE constructed of a carbon fiber disc having a RASA of approximately 57.23 mm², with an average current of 100 to 300 uA, which further comprises approximately $1.8 \times 10^{16}$ ASM active sites. The sensing material further comprises a disc-shaped AIM comprising a RASA of approximately 57.41 mm².

The ASM of the planar sensing material was tested at a scan rate of 60 mV/s with amplitude of 100 mV at a frequency of 60 Hz. The AIM of the sensing material was tested at a scan rate of 30 mV/s with amplitude of 25 mV at a frequency of 60 Hz. The average signal intensity/current generated by the ASM is 300 uA, with an average current density of approximately 5.34 A/m$^2$. The average signal intensity/current generated by the AIM is 400 uA, with an average current density of approximately 6.97 A/m$^2$.

In some embodiments, the planar sensing material comprises a minimum useful life of 21 days, and may exceed 1000 hours of use when stored dry at 25° C.

Example 9: Assembly of Hybrid Sensor

Figure 24:
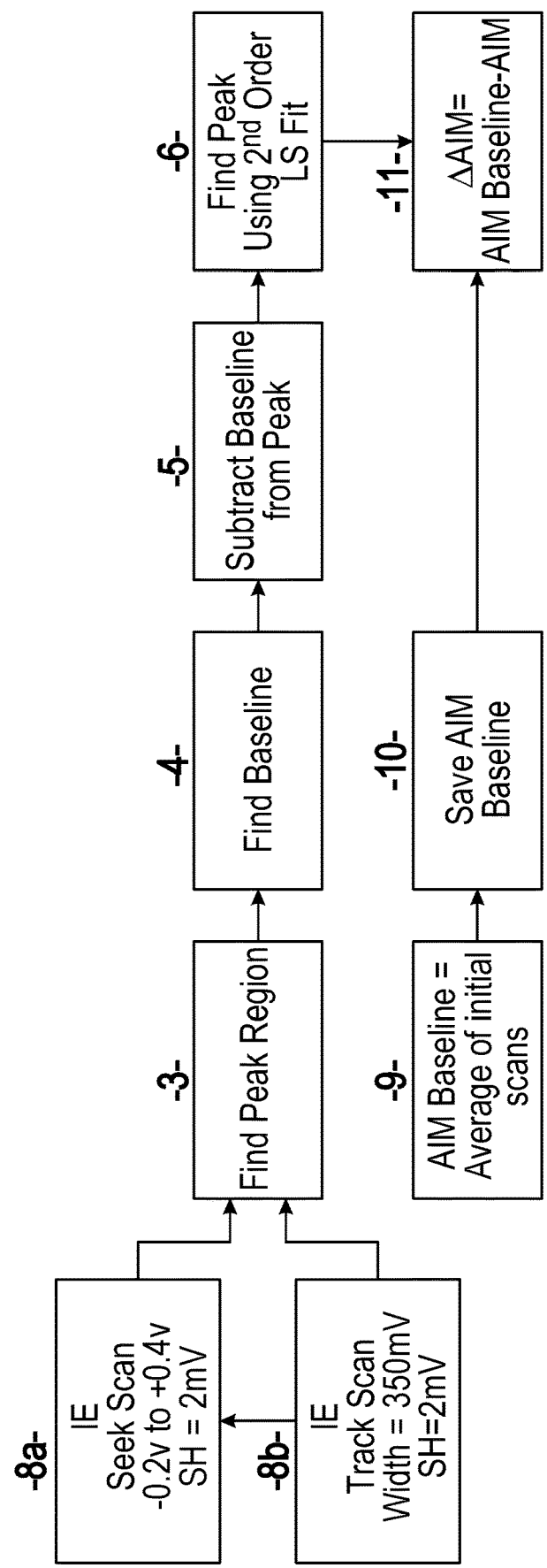
FIG. 24 is a schematic demonstrating the process for assembling a representative sensor probe assembly in accordance with an embodiment of the present invention.
Figure 25:
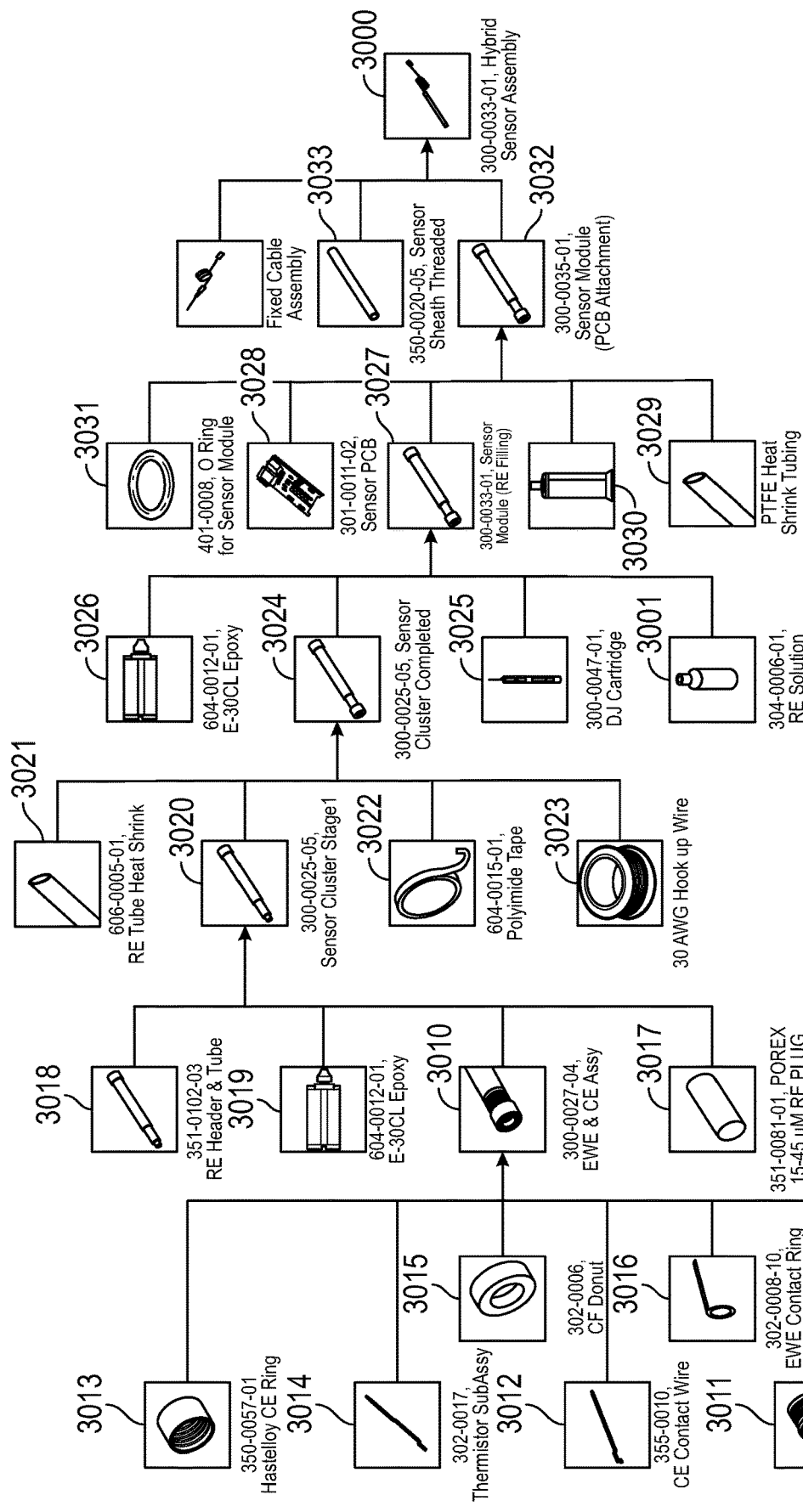

A hybrid sensor assembly 3000 is assembled as described herein and as shown in FIG. 24. A WE and RE assembly 3010 is assembled by first attaching CE contact wire 3012, thermistor subassembly 3014, and WE contact ring 3016 onto WE and RE housing 3011, such that electrical leads of CE contact wire 3012, thermistor subassembly 3014, and WE contact ring 3016 extend outwardly from the proximal end of housing 3011. CE ring 3013 is fitted over the outer distal end of housing 3011 and CE insulator 3015 is inserted into the distal opening of housing 3011. RE plug 3017 is inserted into the proximal opening of housing 3011 and held by friction fit. Assembly 3010 is then threadedly secured to RE Header and Tube 3018, and secured thereto via an epoxy 3019 to provide sensor cluster 3020. The contact leads of the various components are further isolated and/or insulated using heat shrink tube 3021 and polyimide tape 3022 while the electrical connections are made using 30 AWG wire 3023 to provide a completed cluster assembly 3024.

The RE cartridge 3025 is inserted within the proximal end of assembly 3024 and adhered therein via an epoxy 3026. Cartridge 3025 is then filled with RE solution 3001 to provide sensor module 3027. Module 3027 is further fitted with a sensor printed circuit board (PCB) 3028 which is operably coupled to wire leads 3023 and then insulated via heat shrink tube 3029. PCB 3028 is adhered to module 3027 via a non-conductive epoxy 3030. An O-ring 3031 is fitted over tube 3018 and positioned against CE ring 3013 to provide completed sensor module 3032. Sensor module 3032 is then threadedly inserted within sensor sheath, housing or handle 3033. Finally, cable assembly 3034 is coupled to PCB 3028 at the proximal end of module 3032 to provide hybrid sensor assembly 3000.

The invention claimed is:

1. An analyte sensing device, comprising:
    an analyte sensor comprising one or more solid-state electrodes, each electrode having a redox active surface area (RASA), the RASA comprising at least one of an analyte sensitive material (ASM) and an analyte insensitive material (AIM) incorporated into a cross-linked hydrogel matrix material that is non-covalently attached to the RASA, the one or more solid-state electrodes having a physical parameter selected from the group consisting of: i) an exposed surface area of the RASA of from 3 mm$^2$ to 15 mm$^2$, from 8 mm$^2$ to 75 mm$^2$, or from 100 mm$^2$ to 400 mm$^2$; and ii) a thickness of the cross-linked hydrogel matrix material of from approximately 0.06 mm to approximately 0.25 mm,
    wherein the physical parameter is configured to generate an output signal within a range of 5 µA to 400 µA when a current density of the solid-state electrode is from approximately 1.0 A/m$^2$ to no greater than 20.0 A/m$^2$, and
    wherein the analyte sensor comprises a working electrode mounted to a top surface of a sensor tip, and an indicator electrode mounted to a bottom surface of the sensor tip, said top and bottom surfaces comprising opposing, flattened surfaces of the sensor tip, and further comprising a reference electrode comprising a distal surface of the sensor tip.

2. The device of claim 1, further comprising a probe having a distal end comprising the analyte sensor.

3. The device of claim 2, wherein the analyte sensor is operably and selectively coupled to the distal end of the probe.

4. The device of claim 1, further comprising a first solid-state electrode comprising an ASM, and a second solid-state electrode comprising an AIM.

5. The device of claim 1, wherein the RASA comprises a three-dimensional structure comprising an arched, half donut-shape.

6. The device of claim 1, wherein the analyte sensor comprises a conventional reference electrode consisting of a Ag/AgCl wire in contact with a KCl solution.

7. The device of claim 1, further comprising a container having a wall surface at least partially surrounding an interior of the container, the RASA of the one or more solid-state electrodes located at least partially within the interior of the device and positioned to contact an item stored in the container.

8. The device of claim 7, wherein the wall surface further comprises an outer wall surface and a wall thickness, and wherein the one or more solid-state electrodes each comprise at least one electrical contact passing through the wall thickness such that a portion of the electrical contact is located on the outer wall surface.

9. The device of claim 8, wherein the container comprises at least one of: a wall thickness of less than 2 mm; a flexible material; a reaction vessel; a cell bag; a bioreactor bag; and a sample plate.

10. The device of claim 7, wherein the container further comprises a mounting surface for receiving the analyte sensor.

11. The device of claim 10, wherein the analyte sensor is coupled to the wall surface via at least one of mechanical interference, threading, welding, plastic welding, glue, adhesive, epoxy, mechanical clamp, and a fastener.

12. The device of claim 7, wherein the analyte sensor comprises an adhesive label, and wherein the container comprises a mounting surface configured to receive the analyte sensor, said mounting surface comprising a flange of the container.

13. The device of claim 1, further comprising:
    a first unit comprising a first analyte sensor comprising one or more solid-state electrodes, each electrode having a RASA;
    a second unit comprising a second analyte sensor comprising one or more solid-state electrodes, each electrode having a RASA; and
    a gap between the first analyte sensor and the second analyte sensor and configured to retain a liquid analyte-containing sample having a small volume.

14. The device of claim 13, wherein the small volume is less than 1 milliliter, less than 1 microliter, less than 1 nanoliter, or less than 1 picoliter, and wherein the liquid analyte-containing sample is retained in the gap by a capillary force.

15. The device of claim 1, further comprising a sample docking device comprising an analyte sensor reader having one or more electrical contacts for operably connecting to one or more solid-state electrodes of the analyte sensing device, the sample docking device further comprising circuitry for receiving an output signal from the one or more solid-state electrodes.

16. The device of claim 1, wherein the RASA comprises a three-dimensional structure comprising a disc-shape.

17. The device of claim 1, wherein the RASA comprises a three-dimensional structure comprising a cylindrical-shape.

18. An analyte sensing device, comprising:
an analyte sensor comprising one or more solid-state electrodes, each electrode having a redox active surface area (RASA), the RASA comprising at least one of an analyte sensitive material (ASM) and an analyte insensitive material (AIM) incorporated into a cross-linked hydrogel matrix material that is non-covalently attached to the RASA, the one or more solid-state electrodes having a physical parameter selected from the group consisting of: i) an exposed surface area of the RASA of from 3 $mm^2$ to 15 $mm^2$, from 8 $mm^2$ to 75 $mm^2$, or from 100 $mm^2$ to 400 $mm^2$; and ii) a thickness of the cross-linked hydrogel matrix material of from approximately 0.06 mm to approximately 0.25 mm,
wherein the physical parameter is configured to generate an output signal within a range of 5 µA to 400 µA when a current density of the solid-state electrode is from approximately 1.0 $A/m^2$ to no greater than 20.0 $A/m^2$,
wherein the analyte sensor comprises a working electrode having a first hemispheric cross-section, and indicator electrode having a second hemispheric cross-section, a reference electrode positioned between the working electrode and the indicator electrode, and a counter electrode surrounding the working electrode, the indicator electrode, and the reference electrode.

19. The device of claim 18, further comprising an insulating material or space between the reference electrode, the working electrode, the indicator electrode, and the counter electrode.

* * * * *